US012582716B2

(12) United States Patent
Leach et al.

(10) Patent No.: US 12,582,716 B2
(45) Date of Patent: Mar. 24, 2026

(54) STABLE, AQUEOUS FORMULATIONS OF ANTIBODIES THAT BIND IL5 RECEPTOR

(71) Applicant: AstraZeneca AB, Sodertalje (SE)

(72) Inventors: William Leach, Gaithersburg, MD (US); Rachael Lewus, Gaithersburg, MD (US); James McGivney, Gaithersburg, MD (US); Kelcy Newell, Gaithersburg, MD (US); Kevin Douglas Stewart, Gaithersburg, MD (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 16/298,474

(22) Filed: Mar. 11, 2019

(65) Prior Publication Data

US 2019/0201535 A1 Jul. 4, 2019

Related U.S. Application Data

(63) Continuation of application No. 14/521,870, filed on Oct. 23, 2014, now abandoned.

(60) Provisional application No. 61/895,143, filed on Oct. 24, 2013.

(51) Int. Cl.

| | |
|---|---|
| ***A61K 39/395*** | (2006.01) |
| ***A61K 9/00*** | (2006.01) |
| ***A61K 47/18*** | (2017.01) |
| ***A61K 47/22*** | (2006.01) |
| ***A61K 47/26*** | (2006.01) |
| ***A61K 47/34*** | (2017.01) |
| ***C07K 16/28*** | (2006.01) |
| *A61K 39/00* | (2006.01) |

(52) U.S. Cl.

CPC ............ *A61K 47/34* (2013.01); *A61K 9/0019* (2013.01); *A61K 39/3955* (2013.01); *A61K 39/39591* (2013.01); *A61K 47/183* (2013.01); *A61K 47/22* (2013.01); *A61K 47/26* (2013.01); *C07K 16/2866* (2013.01); *A61K 2039/505* (2013.01)

(58) Field of Classification Search

None

See application file for complete search history.

(56) References Cited

U.S. PATENT DOCUMENTS

| | | | | |
|---|---|---|---|---|
| 6,171,586 | B1 | 1/2001 | Lam | |
| 6,267,958 | B1 | 7/2001 | Andya | |
| 6,538,111 | B1 | 3/2003 | Koike | |
| 7,179,464 | B2 | 2/2007 | Koike et al. | |
| 7,214,775 | B2 | 5/2007 | Hanai et al. | |
| 7,718,175 | B2 | 5/2010 | Hanai et al. | |
| 7,741,442 | B2 | 6/2010 | Kanda et al. | |
| 8,101,185 | B2 | 1/2012 | Kanda et al. | |
| 9,441,037 | B2 | 9/2016 | Ward et al. | |
| 9,441,046 | B2 | 9/2016 | Ward et al. | |
| 9,441,047 | B2 | 9/2016 | Ward et al. | |
| 2005/0276823 | A1* | 12/2005 | Cini | A61K 47/183 424/400 |
| 2006/0088523 | A1* | 4/2006 | Andya | C07K 16/32 424/133.1 |
| 2007/0048304 | A1 | 3/2007 | Koike et al. | |
| 2009/0162352 | A1 | 6/2009 | Adler | |
| 2009/0304706 | A1 | 12/2009 | Lu et al. | |
| 2010/0074903 | A1 | 3/2010 | Grauschopf et al. | |
| 2010/0291073 | A1 | 11/2010 | Koike et al. | |
| 2012/0014968 | A1 | 1/2012 | Walsh et al. | |
| 2013/0109807 | A1 | 5/2013 | Gagnon | |

FOREIGN PATENT DOCUMENTS

| | | | |
|---|---|---|---|
| CN | 101541345 | A | 9/2009 |
| CN | 102458469 | A | 5/2012 |
| WO | 9704801 | A1 | 2/1997 |
| WO | 2013131987 | A1 | 9/2012 |
| WO | 2013059408 | A1 | 4/2013 |
| WO | 2013063510 | A1 | 5/2013 |
| WO | 2013066780 | A1 | 10/2013 |
| WO | 2013186700 | A1 | 12/2013 |
| WO | 2015023504 | A1 | 2/2015 |
| WO | 2015023504 | A8 | 2/2015 |
| WO | 2015023507 | A2 | 2/2015 |
| WO | 2015023507 | A3 | 2/2015 |

OTHER PUBLICATIONS

International Search Report corresponding to PCT/US14/61997, dated Feb. 15, 2015.

Cambridge Network, 2013, "AstraZeneca advances Medimmune's benralizumab to Phase III in severe asthma", https://www.cambridgenetwork.co.uk/news/medimmunes-benralizumab-to-phase-III/.

Daugherty, Ann L., 2006, "Formulation and delivery issues for monoclonal antibody therapeutics", ScienceDirect, Advanced Drug Delivery Reviews 58:686-706.

Supplementary European Search Report corresponding to EP14855343 dated Jul. 5, 2017.

(Continued)

*Primary Examiner* — Yunsoo Kim

(74) *Attorney, Agent, or Firm* — FINNEGAN, HENDERSON, FARABOW, GARRETT & DUNNER, LLP

(57) ABSTRACT

The present invention relates to stable, aqueous antibody formulations. In some embodiments, the stable, aqueous formulations comprise about 2 mg/mL to about 100 mg/mL of an anti-IL5R antibody, and about 0.002% to about 0.01% polysorbate-20. Also provided are methods of making and methods of using such antibody formulations.

27 Claims, 24 Drawing Sheets

Specification includes a Sequence Listing.

(56) References Cited

OTHER PUBLICATIONS

Narasimhan, Chakravarthy et al., 2012, High-dose monoclonal antibodies via the subcutaneous route: challenges and technical solutions, an industry perspective, Therapeutic Delivery, 3(7):889-900.
Agarkhed, M., et al., "Effect of Polysorbate 80 Concentration on Thermal and Photostability of a Monoclonal Antibody," *AAPS PharmSciTech* 14(1):1-9, American Association of Pharmaceutical Scientists, United States (2012).
Ahmed, L., et al., "Intrinsic physicochemical profile of marketed antibody-based biotherapeutics," *PNAS* 118(37):1-11, United States National Academy of Sciences, United States (2021).
Awwad, S., and Angkawinitwong, U., "Overview of Antibody Drug Delivery," *Pharmaceutics* 10(83):1-24, MDPI, Switzerland (2018).
Basu, P., et al., "$IgG_1$ Aggregation and Particle Formation Induced by Silicone-Water Interfaces on Siliconized Borosilicate Glass Beads: A Model for Siliconized Primary Containers," *Journal of Pharmaceutical Sciences* 102(3):852-865, Wiley Periodicals, Inc. and the American Pharmacists Association (2013).
Carpenter, J.F., at al., "Separation of Freezing-and Drying-Induced Denaturation of Lyophilized Proteins Using Stress-Specific Stabilization," *Archives of Biochemistry and Biophysics* 303(20):456-464, Academic Press, Inc., United States (1993).
Carpenter, J.F., et al., "Overlooking Subvisible Particles in Therapeutic Protein Products: Gaps that may Compromise Product Quality," Author Manuscript, *J. Pharm Sci.* 98(40):1201-1205, Wiley-Liss, Inc. and the American Pharmacists Association, United States (2009).
Chang, B.S., et al., "Surface-Induced Denaturation of Proteins during Freezing and Its Inhibition by Surfactants," *Journal of Pharmaceutical Sciences* 85(12):1235-1330, American Chemical Society and American Pharmaceutical Association, United States (1996).
Dengl, S., et al., "Aggregation and Chemical Modification of Monoclonal Antibodies under Upstream Processing Conditions," *Pharm Res* 30:1380-1399, Springer Science+Business Media, United States (2013).
Doshi, N. et al., "Understanding Particle Formation: Solubility of Free Fatty Acids as Polysorbate 20 Degradation Byproducts in Therapeutic Monoclonal Antibody Formulation," *Mol. Pharmaceuticals* 12:3792-3804, American Chemical Society, United States (2015).
Garber, E. and Demarest, S.J., "A Broad Range of Fab Stabilities Within a Host of Therapeutic IgGs," *Biochemical and Biophysical Research Communications* 355:751-757, Elsevier, Netherlands (2007).
Garidel, P., et al., "A Thermodynamic Analysis of the Binding Interaction Between Polysorbate 20 and 80 with Human Serum Albumins and Immunoglobulins: A Contribution to Understand Colloidal Protein Stabilisation," *Biophysical Chemistry* 143:70-78, Elsevier, Netherlands (2009).
Hawe, A. and Freiß, W., "Formulation Development for Hydrophobic Therapeutic Proteins," *Pharmaceutical Development and Technology* 12(3):223-237, Informa Healthcare, United States (2007).
Hawe, A., et al., "Fluorescent Molecular Rotors as Dyes to Characterize Polysorbate-containing IgG Formulations," *Pharmaceutical Research* 27(2):314-326, SpringerLink, Germany (2010).
Hillgren, A. and Alden, M., "A Comparison Between the Protection of LDH During Freeze-Thawing by PEG 6000 and Brij 35 At Low Concentrations," *International Journal of Pharmaceuticals* 244:137-149, Elsevier Science B.V., Netherlands (2002).
Izutsu, K., et al., "Stabilizing Effect of Amphiphilic Excipients on the Freeze-Thawing and Freeze-Drying of Lactate Dehydrogenase," *Biotechnology and Bioengineering* 43(11):1102-1107, John Wiley & Sons, Inc., United States (1994).
Jorgensen, L., et al., "Recent Trends in Stabilising Peptides and Proteins in Pharmaceutical Formulation—Considerations in the Choice of Excipients," *Expert Opinion on Drug Delivery* 6(11):1219-1230, Informa UK (2009).
Katz, J.S., et al., "Emerging Challenges and Innovations in Surfactant-Mediated Stabilization of Biologic Formulations," Journal of Pharmaceutical Sciences, Elsevier Inc., Netherlands (2021).
Kerwin, B.A. "Polysorbates 20 and 80 Used in the Formulation of Protein Biotherapeutics: Structure and Degradation Pathways, " *Journal of Pharmaceutical Sciences* 97(8):2924-2935, Wiley-Liss, Inc. and the American Pharmacists Association, United States (2008).
Kessler, M., et al., "Immunogenicity of Biopharmaceuticals," *Nephrol Dial Transplant* 21(5):v9-v12, Oxford University Press, United Kingdom (2006).
Khan, T.A., et al., "Key Interactions of Surfactants in Therapeutic Protein Formulations: A Review," *European Journal of Pharmaceutics and Biopharmaceutics* 97:60-67, Elsevier B.V., Netherlands (2015).
Kiese, S., et al., "Shaken, Not Stirred: Mechanical Stress Testing of an IgG1 Antibody," *J Pharm Sci* 97(10):4347-4366, Wiley-Liss, Inc. and the American Pharmacists Association (2008).
Kishore, R.S., et al., "Degradation of Polysorbates 20 and 80: Studies on Thermal Autoxidation and Hydrolysis," *J Pharm Sci* 100(2):721-731, Wiley-Liss, Inc. and the American Pharmacists Association (2011).
Kishore, R.S., et al., "The Degradation of Polysorbates 20 and 80 and its Potential Impact on the Stability of Biotherapeutics," *Pharm Res* 28:1194-1210, Springer Science+Business Media, LLC, Germany (2011).
Kreilgaard, L., et al., "Effect of Tween 20 on Freeze-Thawing- and Agitation-Induced Aggregation of Recombinant Human factor XIII," *Journal of Pharmaceutical Sciences* 87(12):1597-1603, American Chemical Society and American Pharmaceutical Association, United States (1998).
Kumru, O., et al., "Compatibility, Physical Stability, and Characterization of an IgG4 Monoclonal Antibody After Dilution into Different Intravenous Administration Bags," *J Pharm Sci* 101(10):3636-3650, Wiley-Liss, Inc. and the American Pharmacists Association (2012).
Lam, X..M. et al., "Site-Specific Tryptophan Oxidation Induced by Autocatalytic Reaction of Polysorbate 20 in Protein Formulation," *Pharm Res* 28:2543-2555, Springer Science+Business Media, LLC, Germany (2011).
Le Basle, Y., et al., "Physicochemical Stability of Monoclonal Antibodies: A Review," *Journal of Pharmaceutical Sciences* 109:169-190, Elsevier, Netherlands (2020).
Lee, H.J., et al., "Molecular Origins of Surfactant-Mediated Stabilization of Protein Drugs," *Advanced Drug Delivery Reviews* 63(13):1160-1171, Elsevier, Netherlands (2011).
Maa, Y-F. and Hsu, C.C., "Protein Denaturation by Combined Effect of Shear and Air-Liquid Interface," *Biotechnol Bioeng* 54(6):503-512, John Wiley & Sons, Inc., United States (1997).
Mahler, H-C., et al., "Induction and Analysis of Aggregates ina Liquid IgG1-Antibody Formulation," *European Journal of Pharmaceuticals and Biopharmaceutics* 59:407-417, Elsevier, Netherlands (2005).
Mahler, H-C., et al., "Surface Activity of a Monoclonal Antibody," *J Pharm Sci* 98(12):4525-4533, Wiley-Liss, Inc. and the American Pharmacists Association (2009).
Manning, M.C., "Stability of Protein Pharmaceuticals: An Update," *Pharmaceutical Research* 27(4):544-575, Springer Science+ Business Media, LLC, Germany (2010).
Nema, S. and Avis, K.E., "Freeze-Thaw Studies of a Model Protein, Lactate Dehydrogenase, in the Presence of Cryoprotectants," *Journal of Parenteral Science & Technology* 47(2):76-83, John Wiley & Sons, Inc., United States (1993).
Razinkov, V.I., et al., "Accelerated Formulation Development of Monoclonal Antibodies (mAbs) and mAb-Based Modalities: Review of Methods and Tools," *Journal of Biomolecular Screening*, 20(4):468-483 SAGE Publishing, United States (2015).
Respaud, R., et al., "Effect of Formulation on the Stability and Aerosol Performance of a Nebulized Antibody," *mAbs* 6(5):1347-1355, Taylor & Francis Group, United Kingdom (2014).
Rosenberg, A.S., "Effects of Protein Aggregates: An Immunologic Perspective," *The AAPS Journal* 8(3):E501-E507, Article 59, Springer Science+Business Media, Germany (2006).

(56) References Cited

OTHER PUBLICATIONS

Serno, T., "Inhibition of Therapeutic Protein Aggregation by Cyclodextrins," Dissertation to obtain the Doctoral Degree of Facility of Chemistry and Pharmacy of the Ludwig-Maximilians-Universität München, 297 pages (2010).
Shieh, I.C. and Patel, A.R., "Predicting the Agitation-Induced Aggregation of Monoclonal Antibodies Using Surface Tensiometry," *Mol. Pharmaceutics* 12:3184-3193, ACS Publications, United States (2015).
Shire, S.J., et al., "Challenges in the Development of High Protein Concentration Formulations," *J Pharm Sci* 93(6):1390-1402, Wiley-Liss, Inc. and the American Pharmacists Association (2004).
Singh, S., et al., "Effect of Polysorbate 20 and Polysorbate 80 on the Higher Order Structure of a Monoclonal Antibody and its Fab and Fc Fragments Probed Using 2D NMR Spectroscopy," *J Pharm Sci*, 106(12):3486-3498, Elsevier, Netherlands (2017).
Siska, C.C., et al., "Free Fatty Acid Particles in Protein Formulations, Part 2: Contribution of Polysorbate Raw Material," *J Pharm Sci* 104:447-456, Wiley-Liss, Inc. and the American Pharmacists Association (2015).
Sreedhara, A., et al., "Stability of IgG1 Monoclonal Antibodies in Intravenous Infusion Bags Under Clinical In-Use Conditions," *J Pharm Sci* 101(1):21-30, Wiley-Liss, Inc. and the American Pharmacists Association (2012).
Strickley, R.G. and Lambert, W.J., "A Review of Formulations of Commercially Available Antibodies," *J Pharm Sci* 110:2590-2608, Elsevier, Netherlands (2021).
Thurow, H. and Geisen, K., "Stabilisation of Dissolved Proteins Against Denaturation at Hydrophobic Interfaces," *Diabetologia* 27:212-218, Springer-Verlag, Germany (1984).
Wang, W., "Instability, Stabilization, and Formulation of Liquid Protein Pharmaceuticals," *International Journal of Pharmaceutics* 185:129-188, Elsevier, Netherlands (1999).
Wang, W., et al., "Antibody Structure, Instability, and Formulation," *J Pharm Sci* 96(1):1-26, Wiley-Liss, Inc. and the American Pharmacists Association (2007).
Wang, W., et al., "Protein Aggregation-Pathways and Influencing Factors," *International Journal of Pharmaceutics*, 390:89-99, Elsevier, Netherlands (2010).
Wang, W., et al., "Immunogenicity of Proteins Aggregates—Concerns and Realities," *International Journal of Pharmaceutics*, 431:1-11, Elsevier, Netherlands (2012).
Wang, S., et al., "Stabilizing two IgG1 Monoclonal Antibodies by Surfactants: Balance Between Aggregation Prevention and Structure Perturbation," *European Journal of Pharmaceutics and Biopharmaceutics* 114:23-277, Elsevier, Netherlands (2017).
Webb, S.D., et al., "A New Mechanism for Decreasing Aggregation of Recombinant Human Interferon-γ by a Surfactant: Slowed Dissolution of Lyophilized Formulations in a Solution Containing 0.03% Polysorbate 20," *J Pharm Sci* 91(2):543-558, Wiley-Liss, Inc. and the American Pharmacists Association (2002).
Webb, S.D., et al., "Surface Adsorption of Recombinant Human Interferon-γ in Lyophilized and Spray-Lyophilized Formulations," *J Pharm Sci* 91(6):1474-1487, Wiley-Liss, Inc. and the American Pharmacists Association (2002).
Alberts, B., et al., "The Generation of Antibody Diversity," Chapter 24 in Molecular Biology of The Cell, Fourth Edition, pp. 1385-1392, Garland Science, United States (2002).
Ahmed, L et al., "Intrinsic physicochemical profile of marketed antibody-based biotherapeutics," *Proceedings of the National Academy of Sciences* 118(37): e2020577118 and Supporting Information (2021).
Avastin® (bevacizumab) prescribing label (Sep. 2011), 25 pages.
Dudgeon, K., et al., "General strategy for the generation of human antibody variable domains with increased aggregation resistance," PNAS 109: 10879-10884, National Academy of Sciences, United States (2012).
Kayser, V., et al., "A screening tool for therapeutic monoclonal antibodies: Identifying the most stable protein and its best formulation based on thioflavin T binding," Biotechnology Journal 7: 127-132, Wiley-VCH Verlag GmbH & Co., Germany (2012).
Li, Y., et al., "High Throughput Formulation Screening for Global Aggregation Behaviors of Three Monoclonal Antibodies," Journal of Pharmaceutical Sciences, 100(6): 2120-2135, Wiley-Liss, Inc., United States (2011).
Lowe, D., et al., "Aggregation, Stability, and Formulation of Human Antibody Therapeutics," Advances in Protein Chemistry and Structural Biology 84: 41-61, Elsevier, Inc., Netherlands (2011).
Lucentis® (ranibizumab injection) prescribing label (Mar. 2018), 28 pages.
Maggio, E.T., "Polysorbates, peroxides, protein aggregation, and immunogenicity—a growing concern," Journal of Excipients and Food Chem. 3(2): 45-53, IPEC-Americas Inc., United States (2012).
Mason, B.D., et al., Oxidation of Free L-histidine by tert-Butylhdroperoxide, Pharmaceutical Research 27(3): 447-56, Springer Sciences+Business Media, LLC, Germany (2010).
Raptiva® (efalizumab) prescribing label (Mar. 2009), 36 pages.
Ugwu, S.O. and Apte, S.P., "The Effect of Buffers on Protein Conformational Stability," Pharmaceutical Technology pp. 86-113, Taylor & Francis, United Kingdom (2004).
Wang, X., et al., "Potential aggregation prone regions in biotherapeutics," mAb 1:3, 254-67, Taylor & Francis, United Kingdom (2009).
Wu, S-J., et al., "Structure-based engineering of a monoclonal antibody for improved solubility," Protein Engineering, Design & Selection 23(8): 643-651, Oxford University Press, United Kingdom (2010).
Awotwe-Otoo, D., et al., "Quality by design: Impact of formulation variables and their interactions on quality attributes of a lyophilized monoclonal antibody," Int J Pharm 438(1-2):167-175, Elsevier, Netherlands (Nov. 2012).
Capelle, M.A.H., et al., "High throughput screening of protein formulation stability: practical considerations," Eur J Pharm Biopharm 65(2):131-148, Elsevier, Netherlands (Feb. 2007).
Chen, B., et al., "Influence of histidine on the stability and physical properties of a fully human antibody in aqueous and solid forms," Pharm Res 20(12):1952-1960, Springer Science+Business Media, Germany (Dec. 2003).
Gokarn, Y.R., et al., "Self-buffering antibody formulations," J Pharm Sci 97(8):3051-3066, Elsevier, Netherlands (Aug. 2008).
Goldberg, D.S., et al., "Formulation development of therapeutic monoclonal antibodies using high-throughput fluorescence and static light scattering techniques: role of conformational and colloidal stability," J Pharm Sci 100(4):1306-1315, Elsevier, Netherlands (Apr. 2011).
He, F., et al., "High throughput thermostability screening of monoclonal antibody formulations," J Pharm Sci 99(4):1707-1720, Elsevier, Netherlands (Apr. 2010).
Nema, S., and Brendel, R.J., "Excipients and their role in approved injectable products: current usage and future directions," PDA J Pharm Sci Technol 65(3):287-332, Parenteral Drug Association, United States (May-Jun. 2011).
Uchiyama, S., "Liquid formulation for antibody drugs," Biochim Biophys Acta 1844(11):2041-2052, Elsevier, Netherlands (Nov. 2014).
Warne, N.W., "Development of high concentration protein biopharmaceuticals: the use of platform approaches in formulation development," Eur J Pharm Biopharm 78(2):208-212, Elsevier, Netherlands (Jun. 2011).
Arakawa, T., et al., "Factors affecting short-term and long-term stabilities of proteins," Advanced Drug Delivery Reviews 46(1-3):307-326, Elsevier, Netherlands (Mar. 2001).
Extended European Search Report for European Application No. 20207556.0, Mailed Sep. 9, 2021, 11 Pages.

* cited by examiner

FIG. 1

SEQ ID NO: 1: Variable Light Chain of anti-IL5R
DIQMTQSPSSLSASVGDRVTITCGTSEDIINYLNWYQQKPGKAPKLLIYHTSRLQSGVPSR
FSGSGSGTDFTLTISSLQPEDFATYYCQQGYTLPYTFGQGTKVEIK

SEQ ID NO: 2: Light Chain of anti-IL5R
DIQMTQSPSSLSASVGDRVTITCGTSEDIINYLNWYQQKPGKAPKLLIYHTSRLQSGVPSR
FSGSGSGTDFTLTISSLQPEDFATYYCQQGYTLPYTFGQGTKVEIKRTVAAPSVFIFPPSDE
QLKSGTASVVCLLNNFYPREAKVQWKVDNALQSGNSQESVTEQDSKDSTYSLSSTLTLS
KADYEKHKVYACEVTHQGLSSPVTKSFNRGEC

SEQ ID NO: 3: Variable Heavy Chain of anti-IL5R
EVQLVQSGAEVKKPGASVKVSCKASGYTFTSYVIHWVRQRPGQGLAWMGYINPYNDG
TKYNERFKGKVTITSDRSTSTVYMELSSLRSEDTAVYLCGREGIRYYGLLGDYWGQGTL
VTVSS

SEQ ID NO: 4: Heavy Chain of anti-IL5R
EVQLVQSGAEVKKPGASVKVSCKASGYTFTSYVIHWVRQRPGQGLAWMGYINPYNDG
TKYNERFKGKVTITSDRSTSTVYMELSSLRSEDTAVYLCGREGIRYYGLLGDYWGQGTL
VTVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDSDGSFFLYSKL
TVDKSRWQQGNVFSCSVMHEALHNHYTQKSLSLSPGK

SEQ ID NO: 5: VH CDR1 of anti-IL5R
SYVIH

SEQ ID NO: 6: VH CDR2 of anti-IL5R
YINPYNDGTKYNERFKG

SEQ ID NO: 7: VH CDR3 of anti-IL5R
EGIRYYGLLGDY

SEQ ID NO: 8: VL CDR1 of anti-IL5R
GTSEDIINYLN

SEQ ID NO: 9: VL CDR2 of anti-IL5R
HTSRLQS

SEQ ID NO: 10: VL CDR3 of anti-IL5R
QQGYTLPYT

FIG. 14

| Formulation | Protein Concentration & Fill Configuration | Visible Particles (worst observation) | Monomer Loss by SEC | Sub-visible particles by HIAC (particles/mL) | | Potency |
|---|---|---|---|---|---|---|
| | | | | >10 µm | >25 µm | |
| 130 mM Arginine, 50 mM Trehalose, 20 mM Histidine, 0.02% PS-20, pH 6.0 | 2 g/L, 1 mL PFS | = STD 0 | 0.0%/yr | <590 | <20 | >100% |
| | 2 g/L, 1/2 mL PFS | = STD 0 | 0.0%/yr | <680 | <20 | >100% |
| | 2 g/L, 1/2 mL vial | = STD 1 | 0.0%/yr | <80 | <10 | >100% |
| | 20 g/L, 1 mL PFS | < STD 4 | 0.0%/yr | <2010* | <70 | >97% |
| | 20 g/L, 1/2 mL PFS | T0 testing only | | | | |
| | 20 g/L g, 1/2 mL vial | = STD 1 | 0.1%/yr | | | >100% |
| 250 mM Trehalose, 20 mM Histidine, 0.02% PS-20, pH 6.0 | 20 g/L, 1 mL PFS | = STD 1 | 0.0%/yr | <540 | <20 | >91% |
| | 20 g/L, 1/2 mL PFS | < STD 1 | 0.1%/yr | <230 | <10 | >95% |
| | 20 g/L, 1/2 mL vial | = STD 2 | 0.5 %/yr | <120 | <20 | >100% |
| | 100 g/L, 1 mL PFS | < STD 3 | 0.2 %/yr | <1000 | <40 | >92% |
| | 100 g/L, 1/2 mL PFS | T0 testing only | | | | |
| | 100 g/L, 1/2 mL vial | = STD 1 | 0.4 %/yr | <100 | <30 | >99% |

*One outlier at 2010 particles/mL. Other 6 measurements <820 particles/mL, including 3 measured later than the outlier.

FIG. 17C
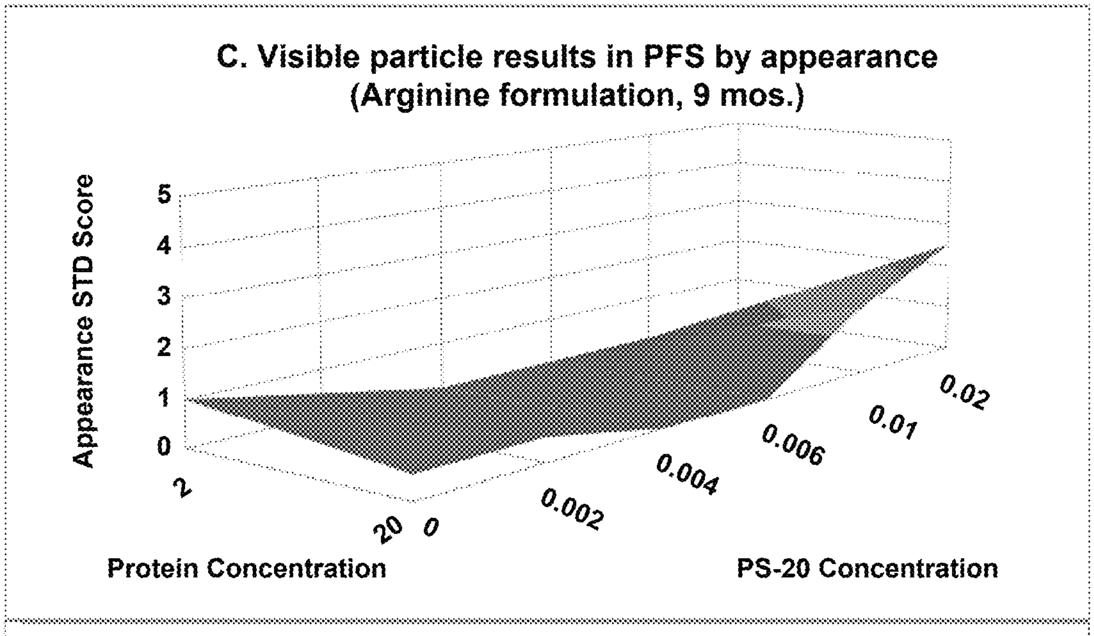
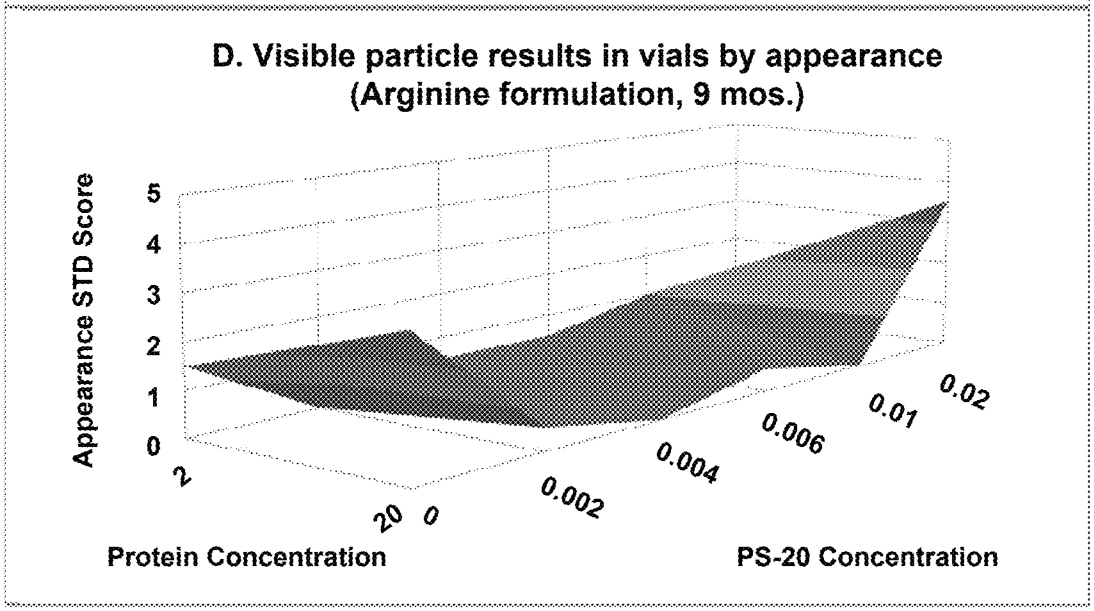
FIG. 17D

FIG. 19A
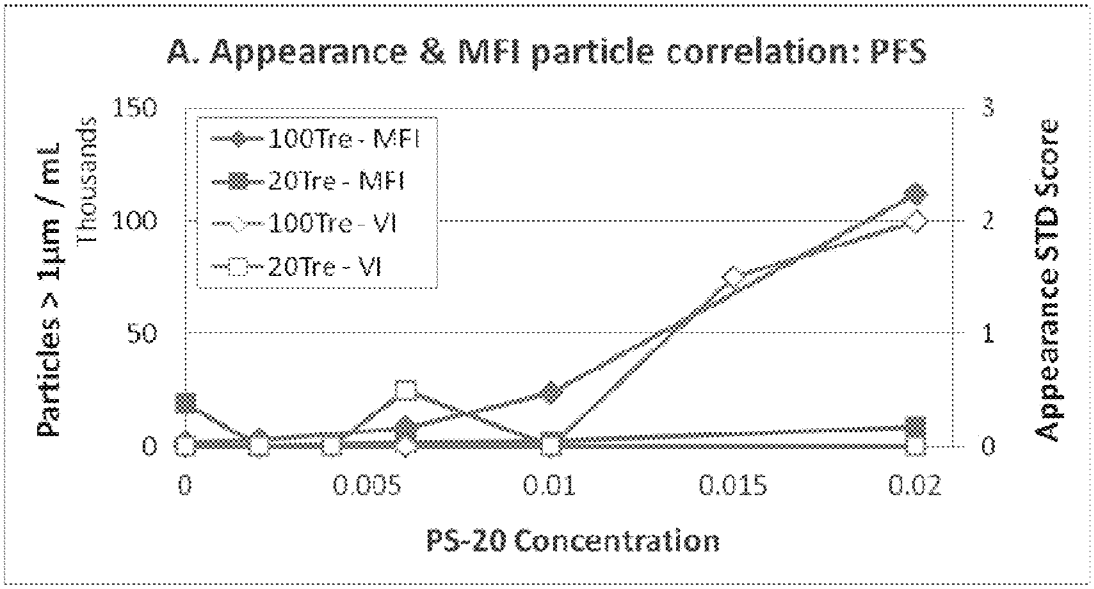
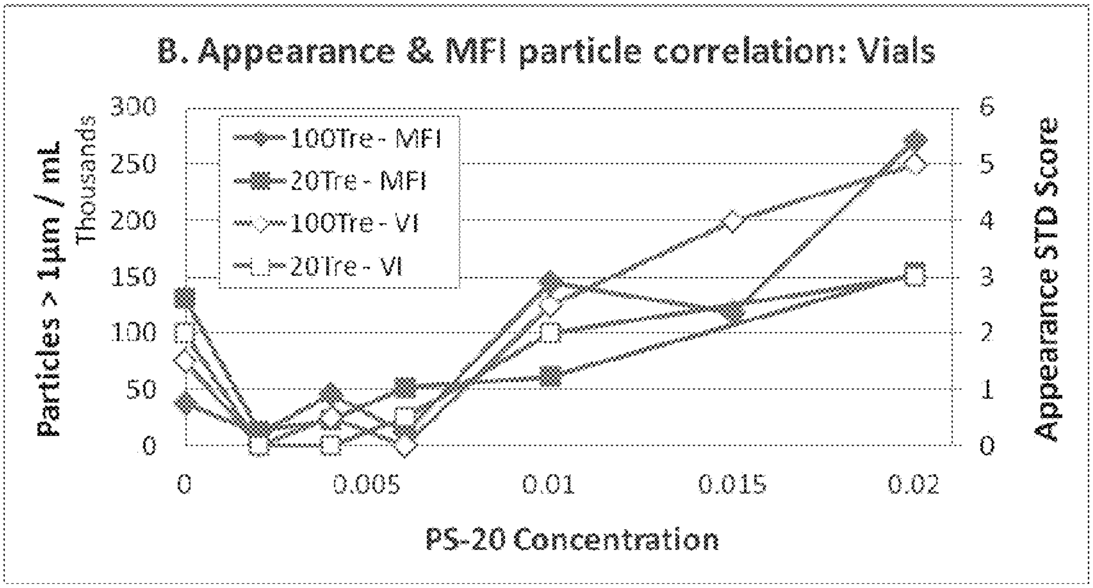
FIG. 19B

SEQUENCE LISTING

```
<160> NUMBER OF SEQ ID NOS: 10

<210> SEQ ID NO 1
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Gly Thr Ser Glu Asp Ile Ile Asn Tyr
            20                  25                  30

Leu Asn Trp Tyr Gln Gln Lys Pro Gly Lys Ala Pro Lys Leu Leu Ile
        35                  40                  45
```

-continued

```
Tyr His Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Leu Pro Tyr
                85                  90                  95

Thr Phe Gly Gln Gly Thr Lys Val Glu Ile Lys
            100                 105
```

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Asp Ile Gln Met Thr Gln Ser Pro Ser Ser Leu Ser Ala Ser Val Gly
1               5                   10                  15

Asp Arg Val Thr Ile Thr Cys Gly Thr Ser Glu Asp Ile Ile Asn Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 3
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Glu Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
            20                  25                  30

Val Ile His Trp Val Arg Gln Arg Pro Gly Gln Gly Leu Ala Trp Met
        35                  40                  45

Gly Tyr Ile Asn Pro Tyr Asn Asp Gly Thr Lys Tyr Asn Glu Arg Phe
    50                  55                  60

Lys Gly Lys Val Thr Ile Thr Ser Asp Arg Ser Thr Ser Thr Val Tyr
65                  70                  75                  80

Met Glu Leu Ser Ser Leu Arg Ser Glu Asp Thr Ala Val Tyr Leu Cys
                85                  90                  95

Gly Arg Glu Gly Ile Arg Tyr Tyr Gly Leu Leu Gly Asp Tyr Trp Gly
            100                 105                 110

Gln Gly Thr Leu Val Thr Val Ser Ser
        115                 120


<210> SEQ ID NO 4
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Ile His Trp Val Arg Gln Arg Pro Gly Gln Gly Leu Ala Trp Met
        35                  40                  45

Gly Tyr Ile Asn Pro Tyr Asn Asp Gly Thr Lys Tyr Asn Glu Arg Phe
    50                  55                  60

Lys Gly Lys Val Thr Ile Thr Ser Asp Arg Ser Thr Ser Thr Val Tyr
65                  70                  75                  80

Met Glu Leu Ser Ser Leu Arg Ser Glu Asp Thr Ala Val Tyr Leu Cys
                85                  90                  95

Gly Arg Glu Gly Ile Arg Tyr Tyr Gly Leu Leu Gly Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255
```

-continued

```
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Tyr Val Ile His
1               5


<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Ile Asn Pro Tyr Asn Asp Gly Thr Lys Tyr Asn Glu Arg Phe Lys
1               5                   10                  15

Gly


<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 7

Glu Gly Ile Arg Tyr Tyr Gly Leu Leu Gly Asp Tyr
1               5                   10


<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Thr Ser Glu Asp Ile Ile Asn Tyr Leu Asn
1               5                   10


<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

His Thr Ser Arg Leu Gln Ser
1               5


<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Gln Gly Tyr Thr Leu Pro Tyr Thr
1               5
```

STABLE, AQUEOUS FORMULATIONS OF ANTIBODIES THAT BIND IL5 RECEPTOR

CROSS REFERENCE TO RELATED APPLICATIONS

This application is a continuation of U.S. application Ser. No. 14/521,870 filed Oct. 23, 2014 which claims benefit under 35 U.S.C. § 119(e) of U.S. Provisional Application No. 61/895,143 filed Oct. 24, 2013. The above listed applications are incorporated by reference herein in its entirety for all purposes.

REFERENCE TO THE SEQUENCE LISTING

This application incorporates by reference a Sequence Listing submitted with this application as text file entitled IL5R-300-US-CNT-Seq-List created on Mar. 11, 2019 and having a size of 9,961 bytes.

FIELD OF THE INVENTION

The present invention relates to stable, aqueous antibody formulations. In some embodiments, the stable, aqueous formulations comprise about 2 mg/mL to about 100 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, and about 0.002% to about 0.01% polysorbate-20. Also provided are methods of making and methods of using such antibody formulations.

BACKGROUND OF THE INVENTION

Antibodies have been used in the treatment of various diseases and conditions due to their specificity of target recognition, thereby generating highly selective outcomes following systemic administration. In order for antibodies to remain effective, they must maintain their biological activity during their production, purification, transport and storage. New production and purification techniques have been developed to provide for large amounts of highly purified monoclonal antibodies to be produced. However, challenges still exist to stabilize these antibodies for transport and storage, and yet even more challenges exist to provide the antibodies in a dosage form suitable for administration.

Denaturation, aggregation, contamination, and particle formation can be significant obstacles in the formulation and storage of antibodies. Due to the wide variety of antibodies, there are no universal formulations or conditions suitable for storage of all antibodies. Optimal formulations and conditions suitable for storage of one antibody are often specific to that antibody. Thus, antibody storage formulations and methods are often a significant part of the research and development process for a commercial antibody.

Various methods have been proposed to overcome the challenges associated with antibody stability. For example, in some instances, the antibody is often lyophilized, and then reconstituted shortly before administration. However, reconstitution is generally not ideal, since it adds an additional step to the administration process, and could introduce contaminants to the formulation. Additionally, even reconstituted antibodies can suffer from aggregation and particle formation. Thus, a need exists to provide stable, aqueous antibody formulations that can overcome the challenges associated with transport and storage.

BRIEF SUMMARY OF THE INVENTION

The present invention is directed to a stable, aqueous antibody formulation comprising: (a) about 2 mg/mL to about 100 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, and (b) about 0.002% to about 0.01% polysorbate-20.

In some embodiments, the antibody formulation further comprises an uncharged excipient. In some embodiments, the uncharged excipient is trehalose. In some embodiments, the uncharged excipient concentration is about 20 mM to about 80 mM. In some embodiments, the uncharged excipient concentration is about 200 mM to about 400 mM.

The antibody can be present in various concentrations. In some embodiments, the formulation comprises about 2 to about 20 mg/ml of the antibody. In some embodiments, the formulation comprises about 20 to about 100 mg/ml of the antibody. In one embodiment, the formulation comprises 30 mg/ml of the antibody.

The formulation can further comprise arginine. In some embodiments, the arginine is L-arginine. In some embodiments, the formulation comprises about 100 mM to about 200 mM L-arginine. In some embodiments, the formulation comprises about 120 mM to about 140 mM L-arginine, and about 40 mM to about 60 mM uncharged excipient. In one embodiment, the formulation comprises about 125 mM L-arginine. In one embodiment, the formulation comprises about 130 mM L-arginine.

In some embodiments, the formulation further comprises histidine. In some embodiments, the histidine concentration is about 15 mM to about 30 mM. In one embodiment, the histidine concentration is about 20 mM.

In some embodiments, the antibody was not subjected to lyophilization.

In some embodiments, the invention is directed to a stable, aqueous antibody formulation comprising about 2 mg/mL to about 100 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, wherein said formulation is stable upon storage at about 40° C. for at least 1 month. In some embodiments, the formulation is stable upon storage at about 25° C. for at least 3 months. In some embodiments, the formulation is stable upon storage at about 5° C. for at least 18 months. In some embodiments, the antibody stored at about 40° C. for at least 1 month retains at least 80% of binding ability to an IL-5R polypeptide compared to a reference antibody which has not been stored. In some embodiments, the antibody stored at about 5° C. for at least 6 months retains at least 80% of binding ability to an IL-5R polypeptide compared to a reference antibody which has not been stored. In some embodiments, the antibody stored at about 40° C. for at least 1 month retains at least 95% of binding ability to an IL-5R polypeptide compared to a reference antibody which has not been stored. In some embodiments, the antibody stored at about 5° C. for at least 6 months retains at least 95% of binding ability to an IL-5R polypeptide compared to a reference antibody which has not been stored. In some embodiments, less than 2% of the antibody forms an aggregate upon storage at about 40° C. for at least 1 month as determined by as determined by HPSEC. In some embodiments, less than 2% of the antibody forms an aggregate upon storage at about 5° for at least 12 months as determined by HPSEC.

In some embodiments, the formulation is substantially free from particles upon storage at about 40° C. for at least 1 month as determined by visual inspection. In some embodiments, the formulation is substantially free from particles upon storage at about 5° C. for at least 12 months as determined by visual inspection.

In some embodiments, the formulation is an injectable formulation. In some embodiments, the formulation is suitable for intravenous, subcutaneous, or intramuscular administration.

In some embodiments, the invention is directed to a sealed container containing an antibody formulation as described herein. In some embodiments, the invention is directed to a pharmaceutical unit dosage form suitable for parenteral administration to a human which comprises an antibody formulation as described herein in a suitable container. In some embodiments, the antibody formulation is administered intravenously, subcutaneously, or intramuscularly. In some embodiments, the suitable container is a pre-filled syringe. In some embodiments, the pre-filled syringe comprises a needle. In some embodiments, the needle is a 29 G thin wall needle. In some embodiments, the pre-filled syringe is a plastic syringe or a glass syringe. In some embodiments, the pre-filled syringe is made of materials that are substantially free from tungsten.

In some embodiments, the pre-filled syringe is coated with silicone. In some embodiments, the pre-filled syringe comprises a plunger having a fluoropolymer resin disk. In some embodiments, the pre-filled syringe comprises (a) about 2 mg/mL to about 20 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, and (b) about 0.002% to about 0.01% polysorbate-20. In some embodiments, the pre-filled syringe further comprises: (c) about 40 mM to about 60 mM trehalose, and (d) about 110 mM to about 150 mM L-arginine. In some embodiments, the invention is directed to a pre-filled syringe comprising: (a) about 20 mg/mL to about 100 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, and (b) about 0.002% to about 0.01% polysorbate-20. In some embodiments, the formulation further comprises: (c) about 200 mM to about 300 mM trehalose.

In some embodiments, the invention is directed to a kit comprising the formulation described herein, the container described herein, the unit dosage forms described herein, or the pre-filled syringes described herein.

In some embodiments, the invention is directed to a stable, aqueous antibody formulation comprising: (a) about 2 mg/mL to about 20 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, (b) about 0.002% to about 0.01% polysorbate-20, (c) about 40 mM to about 60 mM trehalose, (d) about 110 mM to about 150 mM L-arginine, and (e) about 15 to about 30 mM histidine. In one embodiment, the invention is directed to a stable, aqueous antibody formulation comprising: (a) about 2 mg/mL to about 20 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, (b) about 0.006% polysorbate-20, (c) about 50 mM trehalose, (d) about 130 mM L-arginine, and (e) about 20 mM histidine.

In some embodiments, the invention is directed to a stable, aqueous antibody formulation comprising: (a) about 20 mg/mL to about 100 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, (b) about 0.002% to about 0.01% polysorbate-20, (c) about 200 mM to about 300 mM trehalose, and (d) about 15 to about 30 mM histidine. In one embodiment, the invention is directed to a stable, aqueous antibody formulation comprising: (a) about 20 mg/mL to about 100 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, (b) about 0.006% polysorbate-20, (c) about 250 mM trehalose, and (d) about 20 mM histidine. In another embodiment, the invention is directed to a stable, aqueous antibody formulation comprising: (a) about 30 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, (b) about 0.006% polysorbate-20, (c) about 250 mM trehalose, and (d) about 20 mM histidine.

In some embodiments, the invention is directed to a method of producing a stable, aqueous antibody formulation, the method comprising: (a) purifying an antibody to about 1 mg/mL to about 400 mg/mL, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10; (b) placing the isolated antibody in a stabilizing formulation to form the stable, aqueous antibody formulation, wherein the resulting stable, aqueous antibody formulation comprises: (i) about 2 mg/mL to about 100 mg/mL of the antibody, and (ii) about 0.002% to about 0.01% polysorbate-20.

In some embodiments, the invention is directed to a method of making a stable, aqueous antibody formulation, the method comprising: (a) purifying an antibody to about 1 mg/mL to about 400 mg/mL, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10; (b) diluting the antibody to about 2 mg/mL to about 20 mg/mL of the antibody into a solution comprising: (i) about 0.002% to about 0.01% polysorbate-20, (ii) about 40 mM to about 60 mM trehalose, and (iii) about 110 mM to about 150 mM L-arginine.

In some embodiments, the invention is directed to a method of making a stable, aqueous antibody formulation, the method comprising: (a) purifying an antibody to about 1 mg/mL to about 400 mg/mL, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10; (b) diluting the antibody to about 20 mg/mL to about 100 mg/mL of the antibody into a solution comprising: (i) about 0.002% to about 0.01% polysorbate-20, and (ii) about 200 mM to about 300 mM trehalose.

In some embodiments, the invention is directed to a method of producing a reconstituted antibody formulation comprising an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, the method comprising: (a) purifying the antibody from a cell culture; (b) lyophilizing the isolated antibody; (c) adding the lyophilized antibody to a aqueous solution to form a reconstituted antibody formulation, wherein the reconstituted antibody formulation comprises: (i) about 2 mg/mL to about 100 mg/mL of the antibody, and (ii) about 0.002% to about 0.01% polysorbate-20.

In some embodiments, the invention is directed to an antibody formulation comprising an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, wherein the antibody formulation is essentially free of particles. In some embodiments, the antibody formulation comprises an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, wherein the antibody formulation is essentially free of active glutathione S-transferase (GST). In some embodiments, the antibody formulation is essentially free of GST. In some embodiments, the antibody formulation is essentially free of particles for at least 1 month when stored at 38-42° C. In some embodiments, the antibody formulation is essentially free of particles for at least 6 months when stored at 2-6° C. In some embodiments, the antibody formulation is essentially free of particles for at least 18 months when stored at 2-6° C.

In some embodiments, the invention is directed to a method of purifying an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, the method comprising: (a) obtaining a cell culture comprising the antibody, (b) performing affinity chromatography on the antibody (c) performing cation exchange on the antibody, (d) performing mixed-mode chromatography on the antibody. In some embodiments, the method further comprises a viral inactivation process and/or a diafiltration process.

In some embodiments, the invention is directed to a method of treating a pulmonary disease or disorder in a subject, the method comprising administering a therapeutically effective amount of the antibody formulations described herein, the containers described herein, the unit dosage forms described herein, or the pre-filled syringes described herein. In some embodiments, the pulmonary disease or disorder is an eosinophilic disease or disorder. In some embodiments, the pulmonary disease or disorder is asthma, COPD, eosinophilic asthma, combined eosinophilic and neutrophilic asthma, aspirin sensitive asthma, allergic bronchopulmonary aspergillosis, acute and chronic eosinophilic bronchitis, acute and chronic eosinophilic pneumonia, Churg-Strauss syndrome, hypereosinophilic syndrome, drug, irritant and radiation-induced pulmonary eosinophilia, infection-induced pulmonary eosinophilia (fungi, tuberculosis, parasites), autoimmune-related pulmonary eosinophilia, eosinophilic esophagitis, Crohn's disease, or combination thereof. In some embodiments, the pulmonary disease or disorder is asthma. In some embodiments, the pulmonary disease or disorder is chronic obstructive pulmonary disease (COPD).

BRIEF DESCRIPTION OF THE FIGURES

FIG. 1. Amino acid sequences of anti-IL5R antibody.

FIG. 14. The testing plan for stability study #2. All the marked tests will be run on the antibody formulation. Yellow shading indicates the test will be run on the placebo. The notation "ABC" indicates submission for the following tests: potency (BIOASSAY), RP-HPLC, cIEF, non-reduced BioAnalyzer, and reduced BioAnalyzer.

FIG. 19(A-B) is a comparison of Appearance standard scores and MFI results (particles >1 μm) for trehalose formulations in PFS (FIG. 5A) and vials (FIG. 5B). Good agreement is observed for the two methods, which both indicate the acceptable range of PS-20 is 0.002-0.01%.

DETAILED DESCRIPTION OF THE INVENTION

Figure 2:
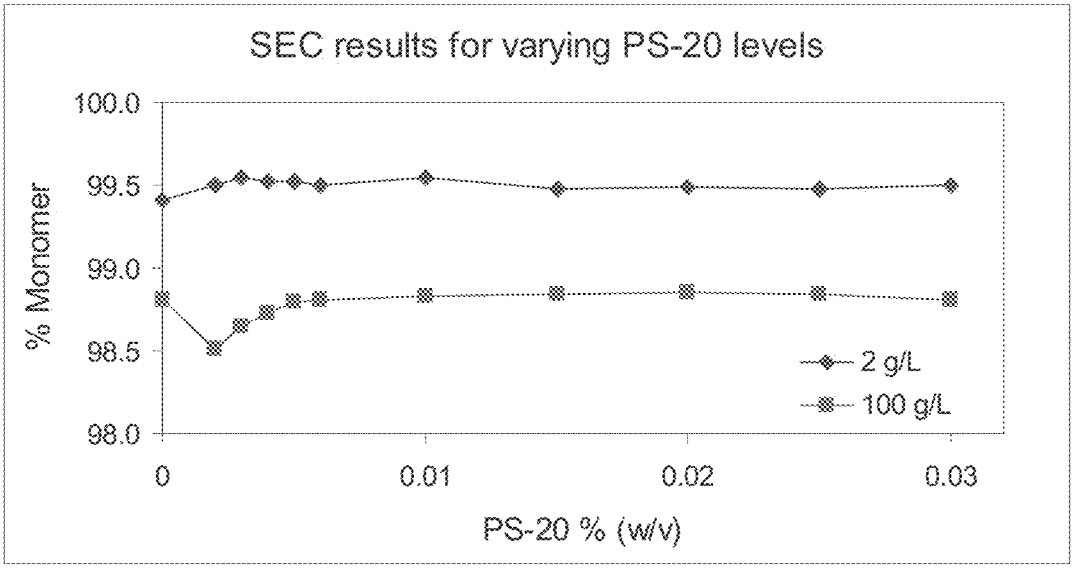
FIG. 2 represents the effect of polysorbate-20 on fraction of monomer in solution. A polysorbate concentration above 0.005% is required to completely maintain the monomer level.

It should be appreciated that the particular implementations shown and described herein are examples, and are not intended to otherwise limit the scope of the application in any way. It should also be appreciated that each of the embodiments and features of the invention described herein can be combined in any and all ways.

The published patents, patent applications, websites, company names, and scientific literature referred to herein are hereby incorporated by reference in their entirety to the same extent as if each was specifically and individually indicated to be incorporated by reference. Any conflict between any references cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise.

Throughout the present disclosure, all expressions of percentage, ratio, and the like are "by weight" unless otherwise indicated. As used herein, "by weight" is synonymous with the term "by mass," and indicates that a ratio or percentage defined herein is done according to weight rather than volume, thickness, or some other measure.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

Technical and scientific terms used herein have the meaning commonly understood by one of skilled in the art to which the present application pertains, unless otherwise defined. Reference is made herein to various methodologies and materials known to those of skilled in the art. Standard reference works setting forth the general principles of recombinant DNA technology include Sambrook et al., "Molecular Cloning: A Laboratory Manual," 2nd Ed., Cold Spring Harbor Laboratory Press, New York (1989); Kaufman et al., Eds., "Handbook of Molecular and Cellular Methods in Biology in Medicine," CRC Press, Boca Raton (1995); and McPherson, Ed., "Directed Mutagenesis: A Practical Approach," IRL Press, Oxford (1991), the disclosures of each of which are incorporated by reference herein in their entireties.

The present invention is directed to stable, aqueous antibody formulations. As described herein, the term "antibody formulation" refers to a composition comprising one or more antibody molecules. The term "antibody" in the present invention is not particularly limited. For clarity, an "antibody" is taken in its broadest sense and includes any immunoglobulin (Ig), active or desired variants thereof, and active or desirable fragments thereof (e.g., Fab fragments, camelid antibodies (single chain antibodies), and nanobodies). The term "antibody" can also refer to dimers or multimers. The antibody can be polyclonal or monoclonal and can be naturally-occurring or recombinantly-produced. Thus, human, non-human, humanized, and chimeric antibodies are all included with the term "antibody." Typically the antibody is a monoclonal antibody of one of the following classes: IgG, IgE, IgM, IgD, and IgA; and more typically is an IgG or IgA.

An antibody of the invention can be from any animal origin including birds and mammals. In some embodiments, the antibody of the methods of the invention are human, murine (e.g., mouse and rat), donkey, sheep, rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins. See, e.g., U.S. Pat. No. 5,939,598 by Kucherlapati et al.

An antibody of the invention can include, e.g., native antibodies, intact monoclonal antibodies, polyclonal antibodies, multispecific antibodies (e.g., bispecific antibodies) formed from at least two intact antibodies, antibody fragments (e.g., antibody fragments that bind to and/or recognize one or more antigens), humanized antibodies, human antibodies (Jakobovits et al., Proc. Natl. Acad. Sci. USA 90:2551 (1993); Jakobovits et al., Nature 362:255-258 (1993); Bruggermann et al., Year in Immunol. 7:33 (1993); U.S. Pat. Nos. 5,591,669 and 5,545,807), antibodies and antibody fragments isolated from antibody phage libraries (McCafferty et al., Nature 348:552-554 (1990); Clackson et al., Nature 352:624-628 (1991); Marks et al., J. Mol. Biol. 222:581-597 (1991); Marks et al., Bio/Technology 10:779-783 (1992); Waterhouse et al., Nucl. Acids Res. 21:2265-2266 (1993)). An antibody purified by the method of the invention can be recombinantly fused to a heterologous polypeptide at the N- or C-terminus or chemically conjugated (including covalently and non-covalently conjugations) to polypeptides or other compositions. For example, an antibody purified by the method of the present invention can be recombinantly fused or conjugated to molecules useful as labels in detection assays and effector molecules such as heterologous polypeptides, drugs, or toxins. See, e.g., PCT publications WO 92/08495; WO 91/14438; WO 89/12624; U.S. Pat. No. 5,314,995; and EP 396,387.

In some embodiments, the antibody formulation of the present invention comprises an anti-IL5 receptor (anti-IL5R) antibody. Antibodies of the present invention specifically bind to an antigen of interest or a fragment thereof, and do not specifically bind to other antigens or fragments thereof. For example, an anti-IL5R antibody will immunospecifically bind to an interleukin-5 receptor polypeptide and does not specifically bind to other polypeptides. Preferably, antibodies or antibody fragments that immunospecifically bind to an IL-5 receptor have a higher affinity to an IL-5 receptor or a fragment of an IL-5 receptor polypeptide when compared to the affinity to other polypeptides or fragments of other polypeptides. The affinity of an antibody is a measure of its binding with a specific antigen at a single antigen-antibody site, and is in essence the summation of all the attractive and repulsive forces present in the interaction between the antigen-binding site of an antibody and a particular epitope. The affinity of an antibody to a particular antigen (e.g., an IL-5 polypeptide or fragment of an IL-5 polypeptide) may be expressed by the equilibrium constant K, defined by the equation K=[Ag Ab]/[Ag][Ab], which is the affinity of the antibody-combining site where [Ag] is the concentration of free antigen, [Ab] is the concentration of free antibody and [Ag Ab] is the concentration of the antigen-antibody complex. Where the antigen and antibody react strongly together there will be very little free antigen or free antibody, and hence the equilibrium constant or affinity of the antibody will be high. High affinity antibodies are found where there is a good fit between the antigen and the antibody (for a discussion regarding antibody affinity, see Sigal and Ron ed., 1994, Immunology and Inflammation—Basic Mechanisms and Clinical Consequences, McGraw-Hill, Inc. New York at pages 56-57; and Seymour et ah, 1995, Immunology—An Introduction for the Health Sciences, McGraw-Hill Book Company, Australia at pages 31-32). Preferably, antibodies or antibody fragments that immunospecifically bind to an IL-5 polypeptide or fragment thereof do not cross-react with other antigens. That is, antibodies or antibody fragments that immunospecifically bind to an IL-5 polypeptide or fragment thereof with a higher energy than to other polypeptides or fragments of other polypeptides (see, e.g., Paul ed., 1989, Fundamental Immunology, 2nd ed., Raven Press, New York at pages 332-336 for a discussion regarding antibody specificity). Antibodies or antibody fragments that immunospecifically bind to an IL-5 polypeptide can be identified, for example, by immunoassays such as radioimmunoassays (RIAs), enzyme-linked immunosorbent assays (ELISAs), and BIAcore assays or other techniques known to those of skill in the art (see, e.g., Seymour et al, 1995, Immunology—An Introduction for the Health Sciences, McGraw-Hill Book Company, Australia at pages 33-41 for a discussion of various assays to determine antibody-antigen interactions in vivo). Antibodies or antibody fragments that immunospecifically bind to an IL-5 polypeptide or fragment thereof only antagonize an IL-5 polypeptide and do not significantly antagonize other activities.

In one embodiment, an IL-5R polypeptide is human IL-5R, an analog, derivative or a fragment thereof. The nucleotide sequence of human IL-5R can be found in the GenBank database (see, e.g., Accession No. M96652.1). The amino acid sequence of human IL-5R can be found in the GenBank database (see, e.g., Accession No. Q01344). Each of these Assession numbers is expressly incorporated by reference herein.

In some embodiments, the antibody formulation comprises an anti-ILSR antibody, for example, a human anti-ILSR antibody. In some embodiments, the anti-ILSR antibody comprises a light chain comprising SEQ ID NO:2 and a heavy chain comprising SEQ ID NO:4. In some further embodiments, the anti-ILSR antibody comprises a light chain variable region comprising SEQ ID NO:1 and a heavy chain variable region comprising SEQ ID NO:3. In a further embodiment, the anti-ILSR antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10. Those of ordinary skill in the art would easily be able to identify Chothia-defined, Abm-defined or other CDRs.

In one embodiment, the anti-ILSR antibody is benralizumab. Information regarding benralizumab (or fragments thereof) for use in the methods provided herein can be found in U.S. Patent Application Publication No. US 2010/0291073 A1, the disclosure of which is incorporated herein by reference in its entirety.

As used herein, the term "analog" or "antibody analog" in the context of an antibody refers to a second antibody, i.e., antibody analog, that possesses a similar or identical functions as the antibody, but does not necessarily comprise a similar or identical amino acid sequence of the antibody, or possess a similar or identical structure of the antibody. An antibody that has a similar amino acid sequence refers to an antibody analog that satisfies at least one of the following: (a) an antibody analog having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of the antibody; (b) an antibody analog encoded by a nucleotide sequence that hybridizes under stringent conditions to a nucleotide sequence encoding the antibody of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, or at least 150 contiguous amino acid residues; and (c) an antibody analog encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding the antibody. An antibody analog with similar structure to the antibody refers to a proteinaceous agent that has a similar secondary, tertiary or quaternary structure to the antibody. The structure of an antibody analog or antibody can be determined by methods known to those skilled in the art, including but not limited to, peptide sequencing, X-ray crystallography, nuclear magnetic resonance, circular dichroism, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. One, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et ah, 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al, 1997, Nucleic Acids Res. 25:3389-3402. Alternatively, PSI-BLAST can be used to perform an iterated search which detects distant relationships between molecules (Id). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM 120 weight residue table, a gap length penally of 12, and a gap penally of 4 can be used.

In some embodiments, the antibody in the antibody formulation is purified prior to being added to the antibody formulation. The terms "isolate," and "purify" refer to separating the antibody from an impurity or other contaminants in the composition which the antibody resides, e.g., a composition comprising host cell proteins. In some embodiments, at least 50%, 70%, 80%, 90%, 95%, 98%, 99%, 99.5%, or 99.9% (w/w) of an impurity is purified from the antibody. For example, in some embodiments, purification of an antibody, e.g. anti-IL5R antibody, would comprise separating the antibody from 99% (w/w) of the host cell proteins present originally in the composition.

In some embodiments, the terms "isolate," and "purify" refer to separating an antibody, e.g. anti-IL5R antibody, from an impurity or other contaminants in the composition to an extent consistent with guidelines of a governmental organization, e.g., the World Health Organization or the United States Food and Drug Administration.

Methods of purifying an antibody are known to those of skill in the art. Suitable techniques for carrying out purification include various types of chromatography, such as affinity chromatography, hydrophobic interaction, ion exchange (such as cation exchange chromatography or mixed-mode chromatography), and filtration.

Affinity chromatography refers to a separation method whereby an antibody, by virtue of its specific binding properties, is bound to an affinity ligand for the antibody. The functional affinity ligand can be immobilized on a solid or semi-solid support so that when a composition comprising the antibody is passed over the ligand and the solid support, the antibody having a specific binding affinity to the ligand adsorbs to the ligand, and one or more other impurities are not adsorbed (or are bound at a lower affinity) and are separated from the antibody. Examples of impurities that do not typically bind (or do not bind well) include process-related impurities (e.g., host cell proteins, DNA, medium components) and some product-related impurities (e.g., antibody fragments). In some embodiments, the solid support comprising the ligand is washed one or more times with a buffer to remove additional impurities before the adsorbed antibody is removed from the ligand and the support. After one or more impurities have been removed, the adsorbed antibody can be removed (eluted) from the ligand and the support, resulting in isolation of the antibody from the original composition. Methods of removing the antibody from the ligand and support are dependent on the ligand and are known to those of skill in the art and can include, e.g., changes in environment, e.g., pH, addition or chaotropic agents or denaturants, or addition of commercially available elution buffers. In some embodiments, more than one affinity purification process can be employed on an antibody composition. Various affinity ligands are known in the art, including Protein A and Protein G (and combinations thereof). Immobilized ligands are commercially available. For example, Protein A affinity systems include MabSelect, MabSelect SuRe, MabSelect Xtra, MabSelect SuRe LX, Sepaharose CL-4B, ProSep vA, ProSep vA Ultra, and Ceramic HyperD.

Ion exchange chromatography includes cation exchange chromatography and mixed chromatography. Cation exchange chromatography refers to any method by which an antibody and some impurity or impurities can be separated based on charge differences using a cation exchange matrix. A cation exchange matrix generally comprises covalently bound, negatively charged groups. Weak or strong cation exchange resins may be employed. Commonly, strong cation exchange resins comprise supported organic groups comprising sulphonic acid or sulphonate groups, depending upon the pH. Weak cation exchanger resins commonly comprise supported organic groups comprising carboxylic acid or carboxylate groups, depending upon the pH. In certain embodiments, multimodal cation exchange resins can be used, which incorporate additional binding mechanisms as well as the ionic interactions, for example one or more of hydrogen bonding interactions and hydrophobic interactions. Examples of suitable cation exchange resins are well known in the art, and can include, but are not limited to Fractogel, carboxymethyl (CM), sulfoethyl (SE), sulfopropyl (SP), phosphate (P) and sulfonate (S), PROPAC WCX-10™ (Dionex), Capto S, S-Sepharose FF, Fractogel EMD $SO_3M$, Toyopearl Megacap II SP 550C, Poros 50 HS, and SP-sepharose matrix. In some embodiments, more than one cation exchange chromatography process can be employed on the composition.

Mixed mode chromatography refers to a method that utilizes more than one form of interaction between the stationary phase and analytes in order to achieve their separation from impurities (e.g., process-related impurities, such as host-cell proteins, DNA, and/or endogenous or adventitious viruses). Examples of suitable anion exchange matrices are known in the art, and can include, but are not limited to, Capto Adhere, Sartobind Q, Natrix Q, Chromasorb Q, and Mustang Q.

In some embodiments, additional filtration steps can be used to remove impurities. For example, in some embodiments nanofiltration or ultrafiltration is used. Nanofiltration comprises passing the composition through a matrix having a pore size of, e.g., less than 75 nm, less than 50 nm, and even less than 15 nm, to separate impurities, e.g., viruses, from the antibody. Commercially available nanofilters and ultrafilters that can be employed are manufactured by various vendors such as Millipore Corporation (Billerica, Mass., e.g., Viresolve Pro and Viresolve Pro+), Pall Corporation (East Hills, N.Y.), GE Healthcare Sciences (Piscataway, N.J.), and Sartorius Corporation (Goettingen, Germany).

In some embodiments, the antibody of the present invention, e.g., an anti-IL5R comprising a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10 is at 1 mg/ml to 200 mg/ml, 2 mg/ml to 100 mg/ml, 2 mg/ml to 30 mg/ml, 2 mg/ml to 25 mg/ml, 2 mg/ml to 20 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, or 20 mg/ml. In some embodiments, the antibody of the present invention, e.g., anti-IL5R, is concentration of about 20 mg/ml, 25 mg/ml, 30 mg/ml, 40 mg/ml, 45 mg/ml, 50 mg/ml, 55 mg/ml, 60 mg/ml, 65 mg/ml, 70 mg/ml, 75 mg/ml, 80 mg/ml, 85 mg/ml, 90 mg/ml, 95 mg/ml, or 100 mg/ml.

The antibody formulation of the present invention can comprise an uncharged excipient. The term excipient refers to a pharmacologically inactive substance formulated with the antibody as described herein. In some embodiments, the excipient can assist in the prevention of denaturation or otherwise assist in stabilizing the antibody. Suitable excipients that may be used in the pharmaceutical compositions are known in the art. Examples can be taken e.g. from the handbook: Gennaro, Alfonso R.: "Remington's Pharmaceutical Sciences", Mack Publishing Company, Easton, Pa., 1990. In some embodiments, the excipient is an "uncharged" excipient, i.e., the excipient does not carry either a positive "+" or negative "−" charge. In some embodiments, the excipient is selected from the group consisting of fructose, glucose, mannose, sorbose, xylose, lactose, maltose, sucrose, dextran, pullulan, dextrin, cyclodextrins, soluble starch, trehalose, sorbitol, erythritol, isomalt, lactitol, maltitol, xylitol, glycerol, lactitol, hydroxyethyl starch, water-soluble glucans.

In some embodiments, the uncharged excipient is about 1 mM to about 1 M, about 2 mM to about 500 mM, about 5 mM to about 400 mM, about 10 mM to about 300 mM or about 20 mM to about 250 mM in the antibody formulation. In some embodiments, the uncharged excipient is about 5 mM to about 150 mM, about 10 mM to about 100 mM, about 20 mM to about 80 mM, about 30 mM, about 40 mM, about 50 mM, about 60 mM, or about 70 mM in the antibody formulation, e.g., an antibody formulation comprising 2 to 20 mg/mL antibody. In one embodiment, the uncharged excipient is about 50 mM in the antibody formulation. In some embodiments, the uncharged excipient is about 50 mM to about 800 mM, about 100 mM to about 500 mM, about 150 mM to about 400 mM, about 200 mM, about 400 mM, about 200 mM, about 300 mM, or about 250 mM in the antibody formulation, e.g., an antibody formulation comprising 20 to 100 mg/mL antibody. In one embodiment, the uncharged excipient is about 250 mM in the antibody formulation.

In some embodiments, the uncharged excipient is trehalose, as represented by the formula:

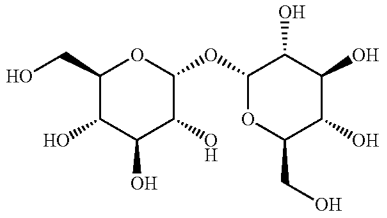 [SMILES: OC[C@H]1O[C@H](O[C@H]2O[C@H](CO)[C@@H](O)[C@H](O)[C@H]2O)[C@H](O)[C@@H](O)[C@@H]1O]

In some embodiments, the trehalose is about 1 mM to about 1 M, about 2 mM to about 500 mM, about 5 mM to about 400 mM, about 10 mM to about 300 mM or about 20 mM to about 250 mM in the antibody formulation. In some embodiments, the trehalose is about 5 mM to about 150 mM, about 10 mM to about 100 mM, about 20 mM to about 80 mM, about 30 mM, about 40 mM, about 50 mM, about 60 mM, or about 70 mM in the antibody formulation, e.g., an antibody formulation comprising 2 to 20 mg/mL antibody. In one embodiment, the trehalose is about 50 mM in the antibody formulation. In some embodiments, the trehalose is about 50 mM to about 800 mM, about 100 mM to about 500 mM, about 150 mM to about 400 mM, about 200 mM, about 400 mM, about 200 mM, about 300 mM, or about 250 mM in the antibody formulation, e.g., an antibody formulation comprising 20 to 100 mg/mL antibody. In one embodiment, the trehalose is about 250 mM in the antibody formulation.

The antibody formulation of the present invention comprises arginine. Arginine is a conditionally non-essential amino acid that can be represented by the formula:

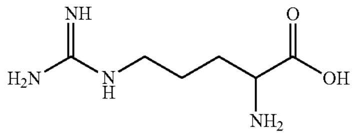 [SMILES: N=C(N)NCCCC(N)C(=O)O]

Arginine, as used herein, can include the free base form of arginine, as well as any and all salts thereof. In some embodiments, arginine includes a pharmaceutically acceptable salt thereof. For example, arginine would include arginine hydrochloride. Arginine, as used herein, also includes all enantiomers (e.g., L-arginine and S-arginine), and any combination of enantiomers (e.g., 50% L-arginine and 50% S-arginine; 90%-100% L-arginine and 10%-0% S-arginine, etc.). In some embodiments, the term "arginine" includes greater than 99% L-arginine and less than 1% S-arginine. In some embodiments, the term "arginine" includes a enantomerically pure L-arginine. In some embodiments, arginine is a pharmaceutical grade arginine.

Various concentrations of arginine can be present in the antibody formulation. In some embodiments, the antibody formulation comprises greater than 50 mM arginine, greater than 75 mM arginine, greater than 100 mM arginine, greater than 125 mM arginine, greater than 130 mM arginine, greater than 150 mM arginine, greater than 175 mM arginine, or greater than 200 mM arginine.

In some embodiments, the antibody formulation comprises up to 800 mM arginine, up to 600 mM arginine, up to 400 mM arginine, up to 200 mM arginine, up to 150 mM arginine, up to 130 mM arginine, or up to 125 mM arginine. In some embodiments, the antibody formulation comprises 50 mM to 300 mM, 75 mM to 250 mM, 100 mM to 200 mM, 110 mM to 160 mM, 120 mM to 150 mM, or about 125 mM arginine. In some embodiments, the antibody formulation comprises 125 mM arginine. In some embodiments, the antibody formulation comprises 130 mM arginine. In some embodiments, arginine is added in an amount sufficient to maintain osmolality of the formulation. In some embodiments, arginine is added in an amount sufficient to achieve a hyper-tonic solution. Applicants have found that in some embodiments, increased ionic strength of the antibody formulations provides increased stability and a reduction in particle formation.

The antibody formulations described herein can have various viscosities. Methods of measuring viscosity of antibody formulations are known to those in the art, and can include, e.g., a rheometer (e.g., Anton Paar MCR301 Rheometer with either a 50 mm, 40 mm or 20 mm plate accessory). In some embodiments of the present invention, the viscosities were reported at a high shear limit of 1000 per second shear rate. In some embodiments, the antibody formulation has a viscosity of less than 20 centipoise (cP), less than 18 cP, less than 15 cP, less than 13 cP, or less than 11 cP. In some embodiments, the antibody formulation has a viscosity of less than 13 cP. One of skill in the art will appreciate that viscosity is dependent on temperature, thus, unless otherwise specified, the viscosities provided herein are measured at 25° C. unless otherwise specified.

The term "injection force" is the amount of pressure (in Newtons) required to pass the antibody formulation through a needle. The injection force is correlated with the amount of resistance provided by the antibody formulation when administering the antibody formulation to a subject. The injection force will be dependent on the gauge of the administering needle, as well as temperature. In some embodiments, the antibody formulation has an injection force of less than 15 N, 12 N, 10 N, or 8 N when passed through a 27 Ga thin wall PFS needle. In some embodiments, the antibody formulation has an injection force of less than 15 N, 12 N, 10 N, or 8 N when passed through a 29 Ga thin wall PFS needle.

The antibody formulations can have different osmolarity concentrations. Methods of measuring osmolarity of antibody formulations are known to those in the art, and can include, e.g., an osmometer (e.g., an Advanced Instrument Inc 2020 freezing point depression osmometer). In some embodiments, the formulation has an osmolarity of between 200 and 600 mosm/kg, between 260 and 500 mosm/kg, or between 300 and 450 mosm/kg.

The antibody formulation of the present invention can have various pH levels. In some embodiments, the pH of the antibody formulation is between 4 and 7, between 4.5 and 6.5, or between 5 and 6. In some embodiments, the pH of the antibody formulation is 5.0. In some embodiments, the pH of the antibody formulation is 6.0. In some embodiments, the pH of the antibody formulation is >7.0. Various means may be utilized in achieving the desired pH level, including, but not limited to the addition of the appropriate buffer.

Various other components can be included in the antibody formulation. In some embodiments, the antibody formulation can comprise a buffer (e.g., histidine, acetate, phosphate or citrate buffer), a surfactant (e.g. polysorbate), and/or a stabilizer agent (e.g. human albumin), etc. In some embodiments, the antibody formulation can comprise pharmaceutically acceptable carriers, including, e.g., ion exchangers, alumina, aluminum stearate, lecithin, serum proteins, such as human serum albumin, buffer substances such as phosphates, sucrose, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, polyethylene-polyoxypropylene-block polymers, and polyethylene glycol. In some embodiments, the antibody formulation further comprises a surfactant. In some embodiments, the surfactant is selected from the group consisting of polysorbate, sodium dodecyl sulfate, and nonionic surfactant.

In some embodiments, the surfactant is polysorbate 20, i.e., polyoxyethylene (20) sorbitan monolaurate, as represented by the formula:

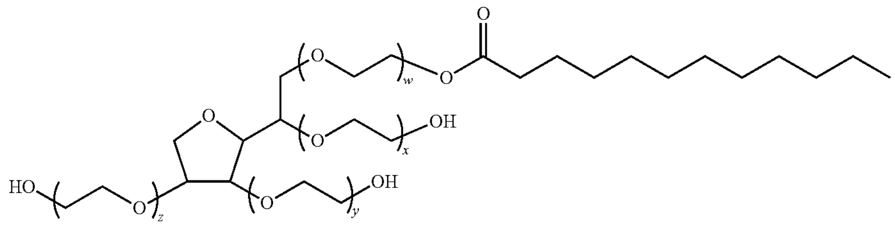

w+x+y+z=20

Polysorbate 20 (PS-20) is available commercially from several commercial vendors, e.g., Alkest® TW 20 (Oxiteno, Brazil), and Tween® 20 (Pierce, Rockford IL). Applicants have found that by carefully controlling the concentration of PS-20 in the antibody formulation, the antibody has added stability and has reduced amounts of particle formation when stored for extended periods of time.

In some embodiments, PS-20 is about 0.001% to about 0.02%, about 0.002% to about 0.015%, about 0.002% to about 0.01%, about 0.004% to about 0.009%, about 0.005% to about 0.008%, about 0.007%, or about 0.006% of the antibody formulation.

In some embodiments, the antibody formulation further comprises histidine. In some embodiments, the antibody formulation comprises about 1 mM to about 100 mM, about 5 mM to about 80 mM histidine, about 10 mM to about 60 mM histidine, about 15 mM to about 50 mM histidine, about 15 mM to about 30 mM histidine, or about 20 mM histidine.

In some embodiments, various components can be omitted from the antibody formulation, or can be "substantially free" of that component. The term "substantially free" as used herein refers to an antibody formulation, said formulation containing less than 0.01%, less than 0.001%, less than 0.0005%, less than 0.0003%, or less than 0.0001% of the designated component.

In some embodiments, the antibody formulation is substantially free of a saccharide, i.e., the antibody formulation, said formulation containing less than 0.01%, less than 0.001%, less than 0.0005%, less than 0.0003%, or less than 0.0001% of a saccharide. The term "saccharide" as used herein refers to a class of molecules that are derivatives of polyhydric alcohols. Saccharides are commonly referred to as carbohydrates and may contain different amounts of sugar (saccharide) units, e.g., monosaccharides, disaccharides and polysaccharides. In some embodiments, the formulation is substantially free of disaccharide. In some embodiments, the formulation substantially free of a reducing sugar, a non-reducing sugar, or a sugar alcohol. In some embodiments, the antibody formulation is substantially free of proline, glutamate, sorbitol, divalent metal ions, and/or succinate.

In some embodiments, the invention is directed to a stable, aqueous antibody formulation comprising: (a) about 2 mg/mL to about 20 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, (b) about 0.002% to about 0.01% polysorbate-20, (c) about 40 mM to about 60 mM trehalose, and (d) about 110 mM to about 150 mM L-arginine. In some embodiments, the formulation further comprises about 20 mM histidine. In one embodiment, the invention is directed to a stable, aqueous antibody formulation comprising: (a) about 2 mg/mL to about 20 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, (b) about 0.006% polysorbate-20, (c) about 50 mM trehalose, (d) about 130 mM L-arginine, and (e) about 20 mM histidine.

In some embodiments, the invention is directed to a stable, aqueous antibody formulation comprising: (a) about 20 mg/mL to about 100 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, (b) about 0.002% to about 0.01% polysorbate-20, (c) about 200 mM to about 300 mM trehalose, and (d) about 20 mM histidine. In one embodiment, the invention is directed to a stable, aqueous antibody formulation comprising: (a) about 20 mg/mL to about 100 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, (b) about 0.006% polysorbate-20, (c) about 250 mM trehalose, and (d) about 20 mM histidine. In another embodiment, the invention is directed to a stable, aqueous antibody formulation comprising: (a) about 30 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, (b) about 0.006% polysorbate-20, (c) about 250 mM trehalose, and (d) about 20 mM histidine.

The antibody formulations of the present invention are an aqueous solution. In some embodiments, the antibody formulation has not been subjected to freezing temperatures, and/or have not been frozen, i.e., they have remained in a liquid state. In some embodiments, the antibody in the antibody formulation has not been subjected to lyophilization.

As used herein, the term "stability" generally is related to maintaining the integrity or to minimizing the degradation, denaturation, aggregation or unfolding of a biologically active agent such as a protein, peptide or another bioactive macromolecule. As used herein, "improved stability" generally means that, under conditions known to result in degradation, denaturation, aggregation or unfolding, the protein (e.g., antibody such as anti-IL5R), peptide or another bioactive macromolecule of interest maintains greater stability compared to a control protein, peptide or another bioactive macromolecule.

In some embodiments, stability refers to an antibody formulation having low to undetectable levels of particle formation. The phrase "low to undetectable levels of particle formation" as used herein refers to samples containing less than 30 particles/mL, less than 20 particles/ml, less than 20 particles/ml, less than 15 particles/ml, less than 10 particles/ml, less than 5 particles/ml, less than 2 particles/ml or less than 1 particle/ml as determined by HIAC analysis or visual analysis. In some embodiments, no particles in the antibody formulation are detected, either by HIAC analysis or visual analysis.

In some embodiments, stability refers to reduced fragmentation of the antibody. The term "low to undetectable levels of fragmentation" as used herein refers to samples containing equal to or more than 80%, 85%, 90%, 95%, 98% or 99% of the total protein, for example, in a single peak as determined by HPSEC, or in two peaks (e.g., heavy- and light-chains) (or as many peaks as there are subunits) by reduced Capillary Gel Electrophoresis (rCGE), representing the non-degraded antibody or a non-degraded fragment thereof, and containing no other single peaks having more than 5%, more than 4%, more than 3%, more than 2%, more than 1%, or more than 0.5% of the total protein in each. The term "reduced Capillary Gel Electrophoresis" as used herein refers to capillary gel electrophoresis under reducing conditions sufficient to reduce disulfide bonds in an antibody.

One of skill in the art will appreciate that stability of a protein is dependent on other features in addition to the composition of the formulation. For example, stability can be affected by temperature, pressure, humidity, pH, and external forms of radiation. Thus, unless otherwise specified, stability referred to herein is considered to be measured at 5° C., one atmosphere pressure, 50% relative humidity, pH of 6.0, and normal background levels of radiation. Stability of the antibody in the antibody formulation can be determined by various means. In some embodiments, the antibody stability is determined by size exclusion chromatography (SEC). SEC separates analytes (e.g., macromolecules such as proteins and antibodies) on the basis of a combination of their hydrodynamic size, diffusion coefficient, and surface properties. Thus, for example, SEC can separate antibodies in their natural three-dimensional conformation from antibodies in various states of denaturation, and/or antibodies that have been degraded. In SEC, the stationary phase is generally composed of inert particles packed into a dense three-dimensional matrix within a glass or steel column. The mobile phase can be pure water, an aqueous buffer, an organic solvent, mixtures of these, or other solvents. The stationary-phase particles have small pores and/or channels which will only allow species below a certain size to enter. Large particles are therefore excluded from these pores and channels, but the smaller particles are removed from the flowing mobile phase. The time particles spend immobilized in the stationary-phase pores depends, in part, on how far into the pores they can penetrate. Their removal from the mobile phase flow causes them to take longer to elute from the column and results in a separation between the particles based on differences in their size.

In some embodiments, SEC is combined with an identification technique to identify or characterize proteins, or fragments thereof. Protein identification and characterization can be accomplished by various techniques, including but not limited chromatographic techniques, e.g., high-performance liquid chromatography (HPLC), immunoassays, electrophoresis, ultra-violet/visible/infrared spectroscopy, raman spectroscopy, surface enhanced raman spectroscopy, mass spectroscopy, gas chromatography, static light scattering (SLS), Fourier Transform Infrared Spectroscopy (FTIR), circular dichroism (CD), urea-induced protein unfolding techniques, intrinsic tryptophan fluorescence, differential scanning calorimetry, and/or ANS protein binding.

In some embodiments, protein identification is achieved by high-pressure liquid chromatography. Various instruments, and apparatuses are known to those of skill in the art to perform HPLC. Generally HPLC involves loading a liquid solvent containing the protein of interest onto a separation column, in which the separation occurs. The HPLC separation column is filled with solid particles (e.g. silica, polymers, or sorbents), and the sample mixture is separated into compounds as it interacts with the column particles. HPLC separation is influenced by the liquid solvent's condition (e.g. pressure, temperature), chemical interactions between the sample mixture and the liquid solvent (e.g. hydrophobicity, protonation, etc.), and chemical interactions between the sample mixture and the solid particles packed inside of the separation column (e.g. ligand affinity, ion exchange, etc.).

In some embodiments, the SEC and protein identification occurs within the same apparatus, or simultaneously. For example, SEC and HPLC can be combined, often referred to as SE-HPLC.

In some embodiments, the aqueous formulation comprises about 2 mg/ml to about 100 mg/ml antibody wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, wherein said formulation is stable upon storage at about 40° C. for at least 1 month. In some embodiments, the formulation is stable upon storage at about 25° C. for at least 3 months. In some embodiments, the formulation is stable upon storage at about 5° C. for at least 6 months. In some embodiments, the formulation is stable upon storage at about 5° C. for at least 12 months. In some embodiments, the formulation is stable upon storage at about 5° C. for at least 18 months. In some embodiments, the formulation is stable upon storage at about 5° C. for at least 24 months, or 36 months.

The term "stable" can be relative and not absolute. Thus, in some embodiments the antibody is stable if less than 20%, less than 15%, less than 10%, less than 5% or less than 2% of the antibody is degraded, denatured, aggregated or unfolded as determined by SEC HPLC when the antibody is stored at 2° C. to 8° C. for 6 months. In some embodiments, the antibody is stable if less than 20%, less than 15%, less than 10%, less than 5% or less than 2% of the antibody is degraded, denatured, aggregated or unfolded as determined by SEC HPLC when the antibody is stored at 2° C. to 8° C. for 12 months. In some embodiments, the antibody in the antibody formulation is stable if less than 20%, less than 15%, less than 10%, less than 5% or less than 2% of the antibody is degraded, denatured, aggregated or unfolded as determined by SEC HPLC when the antibody is stored at 2° C. to 8° C. for 18 months. In some embodiments, the antibody in the antibody formulation is stable if less than 20%, less than 15%, less than 10%, less than 5% or less than 2% of the antibody is degraded, denatured, aggregated or unfolded as determined by SEC HPLC when the antibody is stored at 2° C. to 8° C. for 24 months.

In some embodiments, the antibody is stable if less than 20%, less than 15%, less than 10%, less than 5% or less than 2% of the antibody is degraded, denatured, aggregated or unfolded as determined by SEC HPLC when the antibody is stored at 23° C. to 27° C. for 3 months. In some embodiments, the antibody is stable if less than 20%, less than 15%, less than 10%, less than 5% or less than 2% of the antibody is degraded, denatured, aggregated or unfolded as determined by SEC HPLC when the antibody is stored at 23° C. to 27° C. for 6 months. In some embodiments, the antibody is stable if less than 20%, less than 15%, less than 10%, less than 5% or less than 2% of the antibody is degraded, denatured, aggregated or unfolded as determined by SEC HPLC when the antibody is stored at 23° C. to 27° C. for 12 months. In some embodiments, the antibody is stable if less than 20%, less than 15%, less than 10%, less than 5% or less than 2% of the antibody is degraded, denatured, aggregated or unfolded as determined by SEC HPLC when the antibody is stored at 23° C. to 27° C. for 24 months.

In some embodiments the antibody is stable if less than 6%, less than 4%, less than 3%, less than 2% or less than 1% of the antibody is degraded, denatured, aggregated or unfolded per month as determined by SEC HPLC when the antibody is stored at 40° C. In some embodiments the antibody is stable if less than 6%, less than 4%, less than 3%, less than 2% or less than 1% of the antibody is degraded, denatured, aggregated or unfolded per month as determined by SEC HPLC when the antibody is stored at 5° C.

In some embodiments, the antibody formulations of the present invention can be considered stable if the antibody exhibits very little to no loss of the binding activity of the antibody (including antibody fragments thereof) of the formulation compared to a reference antibody as measured by antibody binding assays know to those in the art, such as, e.g., ELISAs, etc., over a period of 8 weeks, 4 months, 6 months, 9 months, 12 months or 24 months. In some embodiments, the antibody stored at about 40° C. for at least 1 month retains at least 80%, at least about 85%, at least about 90%, at least about 95%, at least about 98%, or at least about 99% of binding ability to an IL-5 receptor polypeptide compared to a reference antibody which has not been stored. In some embodiments, the antibody stored at about 5° C. for at least 6 months retains at least 80%, at least about 85%, at least about 90%, at least about 95%, at least about 98%, or at least about 99% of binding ability to an IL-5 receptor polypeptide compared to a reference antibody which has not been stored. In some embodiments, the antibody stored at about 40° C. for at least 1 month retains at least 95% of binding ability to an IL-5 receptor polypeptide compared to a reference antibody which has not been stored. In some embodiments, the antibody stored at about 5° C. for at least 6 months retains at least 95% of binding ability to an IL-5 receptor polypeptide compared to a reference antibody which has not been stored.

The antibody formulations can provide low to undetectable levels of aggregation of the antibody. The phrase "low to undetectable levels of aggregation" as used herein refers to samples containing no more than about 5%, no more than about 4%, no more than about 3%, no more than about 2%, no more than about 1% and no more than about 0.5% aggregation by weight of protein as measured by high performance size exclusion chromatography (HPSEC) or static light scattering (SLS) techniques. In some embodiments, less than 2% of the antibody forms an aggregate upon storage at about 40° C. for at least 4 weeks as determined by as determined by HPSEC. In some embodiments, less than 2% of the antibody forms an aggregate upon storage at about 5° for at least 3 months, at least 6 months, at least 9 months, at least 12 months, at least 15 months, at least 18 months, at least 24 months, or at least 36 months as determined by HPSEC.

Applicants have found the antibody formulations provided herein result in greatly reduced particle formation as determined by visual inspection, micro-flow imaging (MFI), or size-exclusion chromatography (SEC). In some embodiments, the formulation is substantially free of particles upon storage at about 40° C. for at least 1 month as determined by visual inspection. In some embodiments, the formulation is substantially free from particles upon storage at about 5° C. for at least 6 months, at least 9 months, at least 12 months, at least 15 months, at least 18 months, at least 24 months, or at least 36 months as determined by visual inspection.

In some embodiments, the antibody formulation of the present invention can be used for pharmaceutical purposes. Antibodies used in pharmaceutical applications generally must have a high level of purity, especially in regard to contaminants from the cell culture, including cellular protein contaminants, cellular DNA contaminants, viruses and other transmissible agents. See "WHO Requirements for the use of animal cells as in vitro substrates for the production of biologicals: Requirements for Biological Substances No. 50." No. 878. Annex 1, 1998. In response to concerns about contaminants, The World Health Organization (WHO) established limits on the levels of various contaminants. For example, the WHO recommended a DNA limit of less than 10 ng per dose for protein products. Likewise, the United States Food and Drug Administration (FDA) set a DNA limit of less than or equal to 0.5 pg/mg protein. Thus, in some embodiments, the present invention is directed to antibody formulations meeting or exceeding contaminant limits as defined by one or more governmental organizations, e.g., the United States Food and Drug Administration and/or the World Health Organization.

In some embodiments, the antibody formulation described herein is pharmaceutically acceptable. "Pharmaceutically acceptable" refers to an antibody formulation that is, within the scope of sound medical judgment, suitable for contact with the tissues of human beings and animals without excessive toxicity or other complications commensurate with a reasonable benefit/risk ratio.

Purity of the antibody formulations can vary. In some embodiments, the therapeutic antibody of interest, e.g., anti-IL5R antibody, is greater than 90% (wt/wt) of the total polypeptides present in the antibody formulation. In some embodiments, the therapeutic antibody of interest, e.g., anti-IL5R is greater than 95% (wt/wt), 98% (wt/wt), 99% (wt/wt), 99.5% (wt/wt) or 99.9% (wt/wt) of the total polypeptide present in the antibody formulation.

The formulations as provided herein can be suitable for treatment of a subject. As used herein, "subject" can be used interchangeably with "patient" and refers to any animal classified as a mammal, including humans and non-humans, such as, but not limited to, domestic and farm animals, zoo animals, sports animals, and pets. In some embodiments, subject refers to a human.

The terms "treat" and "treatment" refer to both therapeutic treatment and prophylactic, maintenance, or preventative measures, wherein the object is to prevent or alleviate (lessen) an undesired physiological condition, disorder or disease, or obtain beneficial or desired clinical results. The terms "treat," "treatment," and "treating" refer to the reduction or amelioration of the progression, severity, and/or duration of such a disease or disorder (e.g., a disease or disorder characterized by aberrant expression and/or activity of an IL-5 polypeptide, a disease or disorder characterized by aberrant expression and/or activity of an IL-5 polypeptide or one or more subunits thereof, an autoimmune disease, an inflammatory disease, a proliferative disease, or an infection) or the amelioration of one or more symptoms thereof resulting from the administration of one or more therapies (including, but not limited to, the administration of one or more prophylactic or therapeutic agents). In certain embodiments, such terms refer to reduction in inflammation associated eosinophil-mediated inflammation. In other embodiments, such terms refer to the reduction of the release of inflammatory agents by mast cells, or the reduction of the biological effect of such inflammatory agents. In other embodiments, such terms refer to a reduction of the growth, formation and/or increase in the number of hyperproliferative cells (e.g., cancerous cells). In yet other embodiments, such terms refer to the reduction of inflammation of the airways, skin, gastrointestinal tract, or combinations thereof. In yet other embodiments, such terms refer to the reduction in the symptoms associated with asthma. In some embodiments, such terms refer to the reduction in the symptoms associate with chronic obstructive pulmonary disease (COPD).

The antibody formulation of the present invention can be administered to a subject through various means. In some embodiments, the antibody formulation is suitable for parenteral administration, e.g., via inhalation (e.g., powder or aerosol spray), transmucosal, intravenous, subcutaneous, or intramuscular administration. In some embodiments, the formulation is an injectable formulation. In some embodiments, the invention is directed to a sealed container comprising any of the antibody formulations as described herein.

In some aspects, the present invention is directed to various pharmaceutical dosage forms. Various dosage forms could be applicable to the formulations provided herein. See, e.g., Pharmaceutical Dosage Form: Parenteral Medications, Volume 1, 2$^{nd}$ Edition. In one embodiment, a pharmaceutical unit dosage of the invention comprises the antibody formulation in a suitable container, e.g. a vial or syringe. In one embodiment, a pharmaceutical unit dosage of the invention comprises an intravenously, subcutaneously, or intramuscularly delivered antibody formulation. In another embodiment, a pharmaceutical unit dosage of the invention comprises aerosol delivered antibody formulation. In a specific embodiment, a pharmaceutical unit dosage of the invention comprises a subcutaneously delivered antibody formulation. In another embodiment, a pharmaceutical unit dosage of the invention comprises an aerosol delivered antibody formulation. In a further embodiment, a pharmaceutical unit dosage of the invention comprises an intranasally administered antibody formulation.

The antibody formulations of the present invention can be prepared as unit dosage forms by preparing a vial containing an aliquot of the aqueous antibody formulation for a one-time use. For example, a unit dosage per vial may contain 1 ml, 2 ml, 3 ml, 4 ml, 5 ml, 6 ml, 7 ml, 8 ml, 9 ml, 10 ml, 15 ml, or 20 ml of different concentrations of an antibody that specifically binds to IL5 receptor ranging from about 0.1 mg/ml to about 300 mg/ml. If necessary, these preparations can be adjusted to a desired concentration by adding a sterile diluent to each vial. In a specific embodiment, the aqueous antibody formulations of the present invention are formulated into single dose vials as a sterile liquid that contains about 2 mg/mL to about 20 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, about 0.002% to about 0.01% polysorbate-20, about 40 mM to about 60 mM trehalose, and about 110 mM to about 150 mM L-arginine. In another specific embodiment, the aqueous antibody formulations of the present invention are formulated into single dose vials as a sterile liquid that contains about 20 mg/mL to about 100 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, about 0.002% to about 0.01% polysorbate-20, and about 200 mM to about 300 mM trehalose. In one embodiment, the antibody of the invention is supplied at 2 to 20 mg/ml in 3 cc USP Type I borosilicate amber vials (West Pharmaceutical Services—Part No. 6800-0675). In another embodiment, the antibody of the invention is supplied at 20 to 100 mg/ml in 3 cc USP Type I borosilicate amber vials. The target fill volume is 1.2 mL.

The antibody formulations of the present invention can be prepared as unit dosage forms by preparing a pre-filled syringe containing an aliquot of the aqueous antibody formulation for a one-time use. For example, a unit dosage per pre-filled syringe may contain 0.1 ml, 0.2 ml, 0.3 ml, 0.4 ml, 0.5 ml, 0.6 ml, 0.7 ml, 0.8 ml, 0.9 ml, 1 ml, 2 ml, 3 ml, 4 ml, 5 ml, 6 ml, 7 ml, 8 ml, 9 ml, 10 ml, 15 ml, or 20 ml of different concentrations of an antibody that specifically binds to an IL-5 polypeptide ranging from about 2 mg/ml to about 100 mg/ml. In a specific embodiment, the aqueous antibody formulations of the present invention are formulated into single dose pre-filled syringes as a sterile liquid that contains about 2 mg/mL to about 20 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, about 0.002% to about 0.01% polysorbate-20, about 40 mM to about 60 mM trehalose, and about 110 mM to about 150 mM L-arginine. In a specific embodiment, the aqueous antibody formulations of the present invention are formulated into single dose pre-filled syringes as a sterile liquid that contains about 20 mg/mL to about 100 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, about 0.002% to about 0.01% polysorbate-20, and about 200 mM to about 300 mM trehalose.

Various dosage amounts can be administered in a single use. For example, in some embodiments 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 3 mg, 4 mg, 5 mg, 6 mg, 7 mg, 8 mg, 9 mg, 10 mg, 12 mg, 14 mg, 16 mg, 18 mg, 20 mg, 30 mg, 40 mg, 50 mg, 70 mg, or 100 mg of antibody can be administered in a single dose.

Various types of syringes can be used. The syringe can be filled with the antibody formulation immediately prior to administration to a subject, e.g., less than 1 week, 1 day, 6 hours, 3 hours, 2 hours, 1 hour, 30 minutes, 20 minutes, or 10 minutes prior to administration to a subject. In some embodiments, the syringe is filled with the antibody formulation at the point of retail sale, or by the facility for which treatment of the subject occurs. In some embodiments, the syringe is pre-filled, e.g., the syringe is filled with the antibody formulation greater than 1 day, 2 days, 4 days, 1 week, 2 weeks, 1 month, 2 months, 3 months, 6 months, 12 months, 18 months, 24 months, 3 years, or 4 years prior to administration to a subject. In some embodiments, the pre-filled syringe comprises a needle, e.g., a 27 G regular wall needle, a 27 G thin wall needle, a 29 G regular wall needle, or a 29 G thin wall needle. In some embodiments, the pre-filled syringe comprises a 29 G thin wall needle.

In some embodiments, any syringe suitable for administration to the desired subject can be used. In some embodiments, the syringe is a plastic syringe or a glass syringe. In some embodiments, the syringe is made of materials that are substantially free from tungsten. In some embodiments, the syringe is coated with silicone. In some embodiments, the pre-filled syringe comprises a plunger having a fluoropolymer resin disk. Examples of syringes can include, but are not limited to Hypak™ for Biotech 1 ml Long (Becton Dickinson), with a Becton Dickinson Hypak 1 mL long plunger stopper 4023 Flurotec Daikyo Si1000 (Catalog #47271919), C3Pin (lot # E912701), Hypak™ for Biotech 0.8 mg silicone oil (Becton Dickinson), and CZ syringes (West, Catalog #19550807).

The aqueous antibody formulations of the present invention may be sterilized by various sterilization methods, including sterile filtration, radiation, etc. In a specific embodiment, the difiltered antibody formulation is filter-sterilized with a presterilized 0.2 micron filter. Sterilized aqueous antibody formulations of the present invention may be administered to a subject to prevent, treat and/or manage an immune response, e.g. an inflammatory response.

In some embodiments, the pre-filled syringe comprises (a) about 2 mg/mL to about 20 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, and (b) about 0.002% to about 0.01% polysorbate-20. In some embodiments, the pre-filled syringe further comprises (c) about 40 mM to about 60 mM trehalose, and (d) about 110 mM to about 150 mM L-arginine. In some embodiments, the pre-filled syringe comprises (a) about 20 mg/mL to about 100 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, and (b) about 0.002% to about 0.01% polysorbate-20. In some embodiments, the pre-filled syringe further comprises (c) about 200 mM to about 300 mM trehalose.

In some embodiments, the invention is directed to a kit comprising any of the antibody formulations described herein, the containers described herein, the unit dosage forms described herein, or the pre-filled syringe described herein.

In some embodiments, the present invention can also be directed to a method of producing a stable, aqueous antibody formulation comprising an antibody, the method comprising: (a) purifying an antibody to about 1 mg/mL to about 400 mg/mL, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10; and (b) placing the isolated antibody in a stabilizing formulation to form the stable, aqueous antibody formulation, wherein the resulting stable, aqueous antibody formulation comprises: (i) about 2 mg/mL to about 100 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, and (ii) about 0.002% to about 0.01% polysorbate-20. In some embodiments, the invention is directed to a method of making a stable, aqueous antibody formulation, the method comprising: (a) purifying an antibody to about 1 mg/mL to about 400 mg/mL, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10; (b) diluting the antibody to about 2 mg/mL to about 20 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, into a solution comprising: (i) about 0.002% to about 0.01% polysorbate-20, (ii) about 40 mM to about 60 mM trehalose, and (iii) about 110 mM to about 150 mM L-arginine. In some embodiments, the invention is directed to a method of making a stable, aqueous antibody formulation, the method comprising: (a) purifying an antibody to about 1 mg/mL to about 400 mg/mL, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10; (b) diluting the antibody to about 20 mg/mL to about 100 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, into a solution comprising: (i) about 0.002% to about 0.01% polysorbate-20, (ii) about 200 mM to about 300 mM trehalose, and (iii) about 20 mM histidine.

Although many aspects of the invention are directed to aqueous formulations, it should be noted for the purpose of equivalents that the antibodies or antibody formulations of the invention may be lyophilized if desired. Thus, the invention encompasses lyophilized forms of the formulations of the invention, or lyophilized antibodies which are later reconstituted into an aqueous form. In some embodiments, the invention is directed to a method of producing a reconstituted antibody formulation comprising a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, the method comprising: (a) purifying the antibody from a cell culture; (b) lyophilizing the isolated antibody; (c) adding the lyophilized antibody to a aqueous solution to form a reconstituted antibody formulation, wherein the reconstituted antibody formulation comprises: (i) about 2 mg/mL to about 100 mg/mL of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, and (ii) about 0.002% to about 0.01% polysorbate-20.

In some embodiments, the inventors have found that anti-IL5R antibody formulations having decreased glutathione S-transferase (GST) concentrations result in reduced (e.g., non-detectable) particle formation. Removal of particles is important for avoiding potential immunogenicity as well as limiting impact on product quality. In some embodiments, the GST concentrations are reduced by affinity chromatography. In some embodiments, the GST concentrations are reduced by using a Protein A column. In some embodiments, the Protein A column is MabSelect Sure (GE Healthcare Life Sciences). In some embodiments, the GST concentrations are reduced by using mixed mode chromatography. In some embodiments, the mixed mode column is Capto™ Adhere (GE Healthcare Life Sciences).

In some embodiments, the invention is directed to an antibody formulation comprising an antibody wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, wherein the antibody formulation is essentially free of particles. In some embodiments, the term "essentially free of particles" refer to the absence of visible particles when viewed under a light box. In some embodiments, the term "essentially free of particles" is synonymous with the phrase "low to undetectable levels of particle formation" as described previously. In some embodiments, essentially free of particles refers to samples containing less than 30 particles/mL, less than 20 particles/ml, less than 20 particles/ml, less than 15 particles/ml, less than 10 particles/ml, less than 5 particles/ml, less than 2 particles/ml or less than 1 particle/ml wherein the particles are greater than 25 μm and the particle count is determined by HIAC analysis or visual analysis. In some embodiments, essentially free of particles refers to samples containing 1 to 50 particles/mL, 2 to 40 particles/ml, 3-30 particles/ml, 4 to 25 particles/ml, or 5 to 20 particles/ml wherein the particles are greater than 25 μm and the particle count is determined by HIAC analysis or visual analysis. In some embodiments, the term "visible particles" refers to particles greater than 25 μm.

In some embodiments, essentially free of particles refers to samples containing 1 to 200 particles/mL, 10 to 150 particles/ml, 30-100 particles/ml, or 40 to 80 particles/ml, wherein the particles are greater than 5 μm and the particle count is determined by HIAC analysis or visual analysis. In some embodiments, the term "visible particles" refers to particles greater than 5 μm. In some embodiments, no particles in the antibody formulation are detected, either by HIAC analysis or visual analysis.

In some embodiments, the invention is directed to an antibody formulation comprising an antibody wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, wherein the antibody formulation is essentially free of glutathione S-transferase (GST). Unless specified otherwise, the term "essentially free of glutathione S-transferase" or "essentially free of GST" would encompass a composition lacking active GST (but which could contain inactive GST) as well as a composition which does not have the GST protein, either in active form or inactive form. In some embodiments, the invention is directed to an antibody formulation comprising an antibody wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, wherein the antibody formulation is essentially free of active GST. The term "active GST" refers to GST capable of catalyzing the formation of the thiol group of glutathione (GSH) to an electrophilic compound such as 1-chloro-2,4-dinitrobenzene (CDNB) for form a GS-DNB conjugate. GST or glutathione S-transferase refers to a family of enzymes that are capable of catalyzing numerous reactions, but mainly the conjugation of a reduced glutathione, via a sulfhydryl group, to electrophilic centers, e.g., aromatics, double bonds, C—$Cl_x$, etc. GST monomers are generally in the range of 22-29 kDa, but they can occur as dimers, trimers, and also hetero-dimers (with other proteins). In some embodiments, the term GST refers to a protein that is capable of catalyzing the formation of the thiol group of glutathione (GSH) to 1-chloro-2,4-dinitrobenzene (CDNB) for form a GS-DNB conjugate.

In some embodiments, the invention is directed to an antibody formulation comprising an antibody wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, wherein the antibody formulation is essentially free of particles for at least 1 month, at least 2 months, at least 3 months, at least 4 months, at least 5 months, at least 6 months, at least 8 months, at least 10 months, at least 12 months, or at least 18 months when stored at 38-42° C. In some embodiments, the invention is directed to an antibody formulation comprising an antibody wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, wherein the antibody formulation is essentially free of particles for at least 1 month, at least 2 months, at least 3 months, at least 4 months, at least 5 months, at least 6 months, at least 8 months, at least 10 months, at least 12 months, at least 18 months, at least 24 months, at least 30 months, at least 36 months, or at least 48 months when stored at 2-6° C.

In some embodiments, the antibody formulation is essentially free of GST. In some embodiments, the term "essentially free of GST" refers to an antibody formulation having a GST activity of less than about 0.5 units/mg antibody, less than about 0.3 units/mg antibody, less than about 0.1 units/mg antibody, less than about 0.08 units/mg antibody, less than about 0.05 units/mg antibody, less than about 0.03 units/mg antibody, less than about 0.01 units/mg antibody, less than about 0.005 units/mg antibody, less than about 0.001 units/mg antibody, less than about $5\times10^{-3}$ units/mg antibody, less than about $1\times10^{-4}$ units/mg antibody, less than about $1\times10^{-5}$ units/mg antibody, or less than about 1 $1\times10^{-6}$ units/mg antibody. In some embodiments, the term "essentially free" refers to a level of GST that is non-detectable using common GST detection techniques.

Various methods to determined GST activity are known to those in the art. In some embodiments, the GST activity is determined using a Glutathione (GSH/GSSG/Total) Fluorometric Assay Kit (BioVision, San Francisco CA).

In some embodiments, the invention is directed to a method of purifying an antibody comprising a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, the method comprising (i) obtaining a cell culture comprising the antibody, (ii) performing affinity chromatography on the antibody, (iv) performing cation exchange on the antibody, (v) performing mixed mode chromatography on the antibody. In some embodiments, the invention is directed to a method of purifying an antibody wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, the method comprising (i) obtaining a cell culture comprising the antibody, (ii) binding the antibody to a Protein A column, (iii) eluting the antibody from the Protein A column, (iv) performing cation exchange on the antibody, (v) performing mixed mode chromatography on the antibody. In some embodiments, the method of purifying an antibody further comprises a viral inactivation process. In some embodiments, the viral inactivation step is performed by lowering the pH to less than 4.0. In some embodiments, the method further comprises a diafiltration process. In some embodiments, the method further comprises a filtration process. In some embodiments, the filtration process is sufficient to remove active virus particles.

In some embodiments, the invention is directed to a method of treating a patient. In some embodiments, the method comprises administering the antibody formulations described herein, the containers described herein, the unit dosage forms described herein, or the pre-filled syringe described herein to a subject in need thereof.

In some embodiments, the invention is suitable for treatment of pulmonary disease or disorder by administering the antibody formulation described herein. In some embodiments, the invention is directed to a method of treating a patient with an eosinophilic disease or disorder by administering the antibody formulation described herein. In some embodiments, the invention is directed to a method of treating a pulmonary disease or disorder in a subject, the method comprising administering the antibody formulations described herein. In some embodiments, the invention is directed to a method of treating an eosinophilic disease or disorder in a subject, the method comprising administering the antibody formulations described herein. In some embodiments, the invention is directed to treatment of pulmonary diseases or disorders e.g., asthma, COPD, eosinophilic asthma, combined eosinophilic and neutrophilic asthma, aspirin sensitive asthma, allergic bronchopulmonary aspergillosis, acute and chronic eosinophilic bronchitis, acute and chronic eosinophilic pneumonia, Churg-Strauss syndrome, hypereosinophilic syndrome, drug, irritant and radiation-induced pulmonary eosinophilia, infection-induced pulmonary eosinophilia (fungi, tuberculosis, parasites), autoimmune-related pulmonary eosinophilia, eosinophilic esophagitis, or Crohn's disease or combination thereof in a subject, the method comprising administering the antibody formulations described herein. In some embodiments, the invention is directed to treatment of asthma in a subject, the method comprising administering the antibody formulations described herein. In some embodiments, the invention is directed to treatment of COPD in a subject, the method comprising administering the antibody formulations described herein.

In some embodiments, a therapeutically effective amount of the antibody formulations described herein is administered to treat a condition. As used herein, the term "therapeutically effective amount" refers to the amount of a therapy (e.g., an antibody that immunospecifically binds to an IL-5 receptor polypeptide), that is sufficient to reduce the severity of a disease or disorder (e.g., a disease or disorder characterized by aberrant expression and/or activity of an IL-5 polypeptide, a disease or disorder characterized by aberrant expression and/or activity of an IL-5 receptor or one or more subunits thereof, an autoimmune disease, an inflammatory disease, a proliferative disease, or an infection (preferably, a respiratory infection) or one or more symptoms thereof), reduce the duration of a respiratory condition, ameliorate one or more symptoms of such a disease or disorder, prevent the advancement of such a disease or disorder, cause regression of such a disease or disorder, or enhance or improve the therapeutic effect(s) of another therapy. In some embodiments, the therapeutically effective amount cannot be specified in advance and can be determined by a caregiver, for example, by a physician or other healthcare provider, using various means, for example, dose titration. Appropriate therapeutically effective amounts can also be determined by routine experimentation using, for example, animal models.

The terms "therapies" and "therapy" can refer to any protocol(s), method(s), and/or agent(s) that can be used in the prevention, treatment, management, or amelioration of a disease or disorder (e.g., a disease or disorder characterized by aberrant expression and/or activity of an IL-5 polypeptide, a disease or disorder characterized by aberrant expression and/or activity of an IL-5 receptor or one or more subunits thereof, an autoimmune disease, an inflammatory disease, a proliferative disease, or an infection (preferably, a respiratory infection) or one or more symptoms thereof). In certain embodiments, the terms "therapy" and "therapy" refer to biological therapy, supportive therapy, and/or other therapies useful in treatment, management, prevention, or amelioration of such a disease or disorder or one or more symptoms known to skilled medical personnel.

As used herein, the term "therapeutic protocol" refers to a regimen for dosing and timing the administration of one or more therapies (e.g., therapeutic agents) that has a therapeutic effective.

The route of administration of the antibody formulation of the present invention can be via, for example, oral, parenteral, inhalation or topical modes of administration. The term parenteral as used herein includes, e.g., intravenous, intraarterial, intraperitoneal, intramuscular, subcutaneous, rectal or vaginal administration. In some embodiments, the antibody is an anti-IL5R antibody and the route of administration is intramuscular injection. While all these forms of administration are clearly contemplated as being within the scope of the invention, in some embodiments, the antibody formulation is suitable for administration via injection, in particular for intravenous or intraarterial injection or drip.

In some embodiments, the compositions and methods of the present invention enable a manufacturer to produce an antibody formulation suitable for administration to a human in a more efficient manner, either by reducing costs, reducing method steps, reducing opportunities for error, reducing opportunities for introduction of unsafe or improper additives, reducing waste, increasing storage time, etc.

EXAMPLES

Example 1

Formulation studies were performed to develop a stable anti-IL5R antibody formulation that is appropriate for delivery of a dose between 2-100 mg via subcutaneous delivery from pre-filled syringe (or a vial back-up configuration). Specifically, two separate antibody concentration formulations were developed, a 2-20 mg/mL formulation, and a 20-100 mg/mL formulation.

1. Materials and Methods a. Source of Anti-IL5R and Preparation of Formulations

Multiple lots of anti-IL5R were used in these studies. All of the lots were produced at various scales by MedImmune and delivered after diafiltration and concentration to approximately 130 g/L in 20 mM histidine/histidine HCl at pH 6. Some lots also had 250 mM trehalose in the diafiltration buffer.

Anti-IL5R was formulated by spiking in excipient addition buffer (EAB) to achieve an anti-IL5R concentration of 100 g/L and appropriate concentrations of buffer and excipient species. Lower concentration drug substances were made from the 100 g/L formulation.

2. Accelerated Stress Methods a. Storage at Increased Temperature

Vials and syringes were stored in controlled stability chambers to maintain constant temperature during storage. The chambers were maintained at 2-8° C., 23-27° C./60% RH, or 38-42° C./75% RH, but will be referred to by their midpoint temperatures of 5°, 25°, or 40° C. henceforth. Vials were stored upright unless otherwise noted and pre-filled syringes were stored tip down.

b. Freeze-Thaw Cycles

Controlled and uncontrolled freeze-thaw cycles were both used in these studies. Uncontrolled freeze-thaw was done by freezing vials in a −40° C. chamber and thawing them at room temperature.

c. Transportation and Shaking

A variety of methods were used to investigate the effect of transportation on anti-IL5R. Benchtop shaking of vials was done by orbital shaking at 150 rpm for 24 hours. Actual transportation was mimicked by shipping the product to an off-site location. The product made two round trips and undergoes ground and air transportation over 4 days. A combination of frozen and cold packs were used to maintain the product temperature at 2-8° C., and was monitored by sensors that indicate temperatures below 0° C. or above 9° C.

For screening studies, transportation was simulated using a vibration table (transportation simulator). The product underwent "air" and "ground" transportation in a similar pattern to that experienced during round trip shipping. The process took 12 hours and again the temperature was controlled with cold packs to be 2-8° C.; sensors were not used. Horizontal orientation was chosen as worst-case orientation during real or simulated shipping due to the potential for bubble travel and potential drug contact with the entire barrel, needle tip and stopper.

3. Experimental Methods a. Methods Following or Deriving from an SOP

Visual inspections were performed by comparing to particle and opalescence standards. Aggregation and fragmentation were monitored by SE-HPLC. For anti-IL5R concentrations below 10 g/L, a larger volume injection was used to achieve similar total protein mass per injection. Some samples were also used for cIEF measurements and RP-HPLC to monitor fragmentation.

b. Protein Concentration

Protein concentration was measured by diluting the protein by serial gravimetric dilution to approximately 0.5 g/L and measuring the absorbance at 280 nm. The concentration was calculated from the extinction coefficient and the dilution factor, and corrected for the effect of density on gravimetric dilution for initial concentrations above 50 g/L.

c. Sub-Visible Particle Counts

Sub-visible particle counts were made using both the MFI and HIAC. For the MFI, 0.9 mL of solution was run neat after the optical illumination was run with water. The first 0.2 mL was used to purge the system and not included in the analysis. An aspect ratio filter of <0.85 was used to remove spherical air bubbles or silicone oil droplets. For HIAC, solutions with concentrations >5 g/L were diluted to approximately 5 g/L, while dilute samples were run neat. The dilution was done inside a laminar flow hood with 20 mM histidine/histidine HCl, pH 6 buffer that was filtered just before use. Samples were degassed under vacuum for at least 30 minutes before testing. The average of three runs was multiplied by the dilution factor for the final result. Silicone oil droplets were not differentiated from protein particles by the HIAC.

4. Data and Discussion a. Polysorbate-20 Concentration Screen

Figure 3:
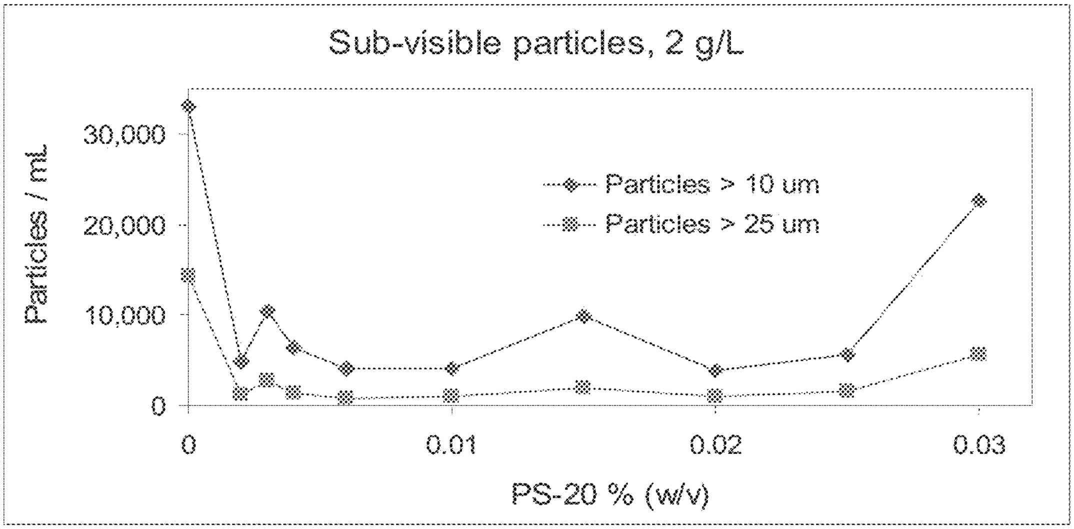
FIG. 3 represents the effect of polysorbate-20 on sub-visible particle counts in 2 g/L solutions. Data for particles >2 μm is not shown but exhibits a similar pattern to the larger particles. The data indicates that sub-visible particle levels in 2 g/L solutions are not controlled by any level of polysorbate.
Figure 4:
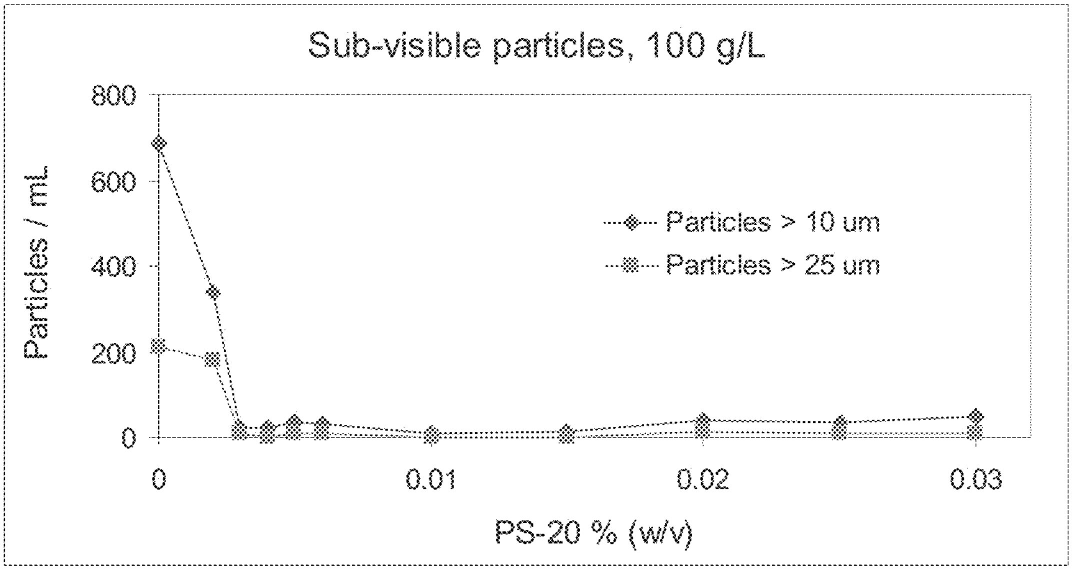
FIG. 4 represents the effect of polysorbate-20 on sub-visible particle counts in 100 g/L solutions. Data for particles >2 μm is not shown but exhibits a similar pattern to the larger particles. The data indicates that polysorbate levels above 0.003% control sub-visible particle levels in 100 g/L solutions.

The first goal was to optimize the PS-20 concentration in the aqueous antibody formulation. Polysorbate was included in solutions to protect the protein from denaturing and aggregating at interfaces, and the required concentration was expected to be different in the liquid product than the lyophilized one. The major interfacial stresses were encountered during freeze-thaw and transportation, so the experimental plan focused on mimicking these. Prior experience indicated that 0.02% polysorbate 20 was sufficient to completely protect against both of these stresses (data not shown). As verification, these stresses were combined in series, in the order expected for clinical production, and an incubation period was added post-stress to enable growth of any potential particles. First, the drug substance underwent three uncontrolled freeze-thaw cycles and the material was filtered and filled into vials. Then it was shaken on the benchtop and incubated for one week at 40° C. before testing by SE-HPLC and MFI. The conditions tested were the extremes of the concentration range, 2 and 100 g/L, formulated in 240 mM trehalose, 20 mM histidine/histidine HCl, pH 6 with varying levels of PS-20 from 0-0.03% w/v. The results are found in FIGS. 2, 3, and 4.

The monomer fraction data indicated that 2 g/L solution remained pure regardless of the polysorbate level, but that low amounts of polysorbate-20, below approximately 0.005%, caused a small amount of aggregation at 100 g/L, but these results did not in themselves indicate an "edge of failure." The stresses utilized were severe, and the degradation level minimal, thus any level of PS-20 tested could be adequate from an SEC aggregate perspective. At 2 g/L, the sub-visible particle counts were quite high and were not controlled by polysorbate-20 in the range tested. At 100 g/L, high sub-visible particle counts were controlled by the presence of 0.003% or more PS-20. Together this data indicated PS-20 levels should be maintained at or above 0.003%.

An alternative method of controlling sub-visible particles was required for low concentration solutions, as is discussed below.

b. Screen of the pH

Figure 5:
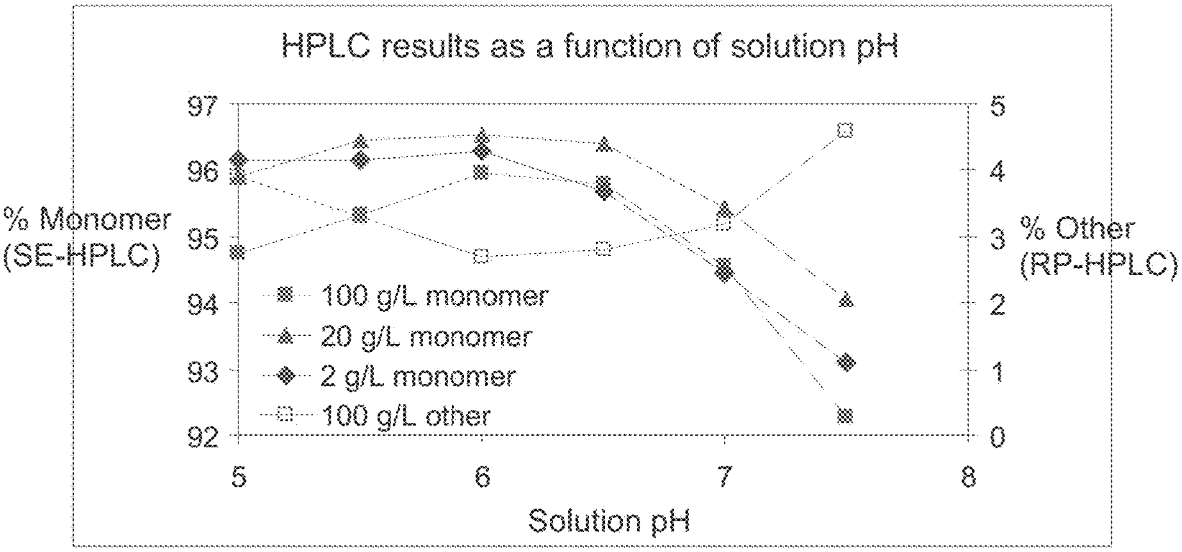
FIG. 5. HPLC monomer (%) and other (%) results as a function of solution pH and protein concentration. Monomer loss is minimized in the pH range of 5.5-6.5.
Figure 6:
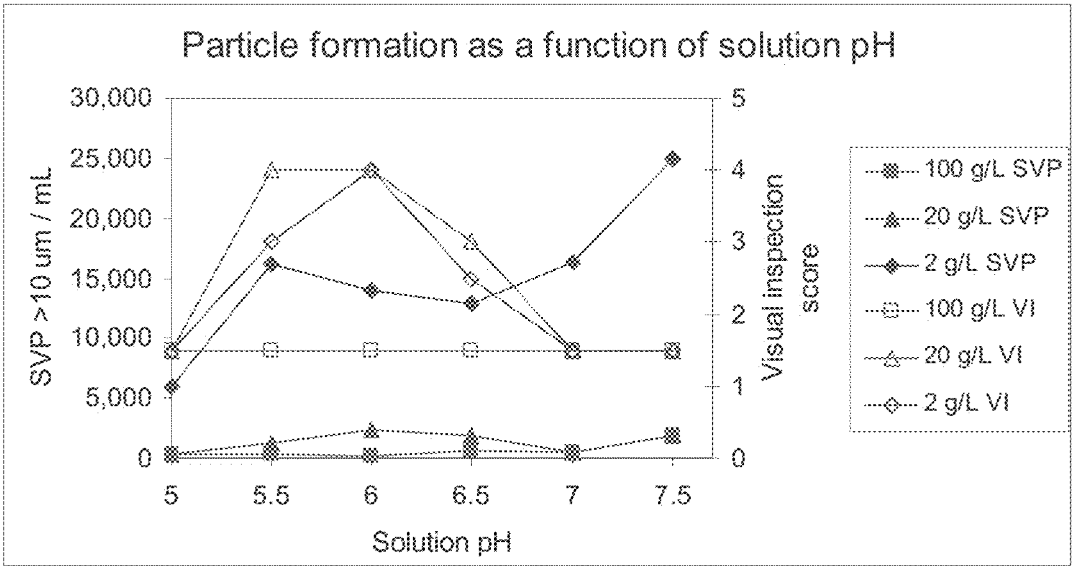
FIG. 6. Particle formation including sub-visible particles >10 μm measured by MFI and visible particles evaluated by comparison to standards as a function of solution pH and protein concentration. Subvisible particles counts are dependent on protein concentration but show no clear trend with pH. More visible particles are observed in the lower protein concentration solutions in the pH range from 5.5-6.5.

The effect of solution pH was studied in 2, 20, and 100 g/L solutions with pH values of 5 to 7.5. The rest of the formulation was constant and included 240 mM trehalose, 20 mM histidine/histidine-HCl, and 0.02% PS-20. Solutions were prepared and stored at 40° C. for one month before testing. Monomer loss by SE-HPLC, subvisible particles by MFI, and visible particles by visual inspection were evaluated for all samples. Additional testing was run on the 100 g/L samples, including RP-HPLC and cIEF. Results are provided in FIGS. 5 and 6.

Aggregation and fragmentation were minimized within the pH range of 5.5-6.5. The results from cIEF were inconsistent with the reference standard at pH 7.0 and above. Sub-visible particle counts were either low or did not show any pattern with solution pH. Visible particle scores were higher from pH 5.5-6.5. Though these scores are high, the samples were inspected close to the light where higher particle counts are routinely seen. It was possible that the source material also contributed to high particle levels, as this was material that had HCP levels reduced by further purification over protein-A. This study indicated that an optimal pH from a particle formation perspective would be pH 5 or pH≥7. However, since the visible particle scores were understood to be overestimates here, the pH was not be changed from pH 6.0 as a result of this study.

c. Effect of Shipping

The formulations needed to be robust to shipping, so they were tested at various protein and PS-20 concentrations in pre-filled syringes. The formulation varied from 2-100 g/L anti-IL5R and 0-0.05% PS-20, with other conditions constant at 240 mM trehalose, 20 mM histidine/histidine HCl, pH 6. A number of other conditions were tested at 2 g/L, including glycine, calcium chloride, pH 5.5, pH 6.5, and 0.02% polysorbate-80. None of these conditions showed improvement over the trehalose formulation at pH 6 with polysorbate-20, so they are not discussed further.

Figure 7:
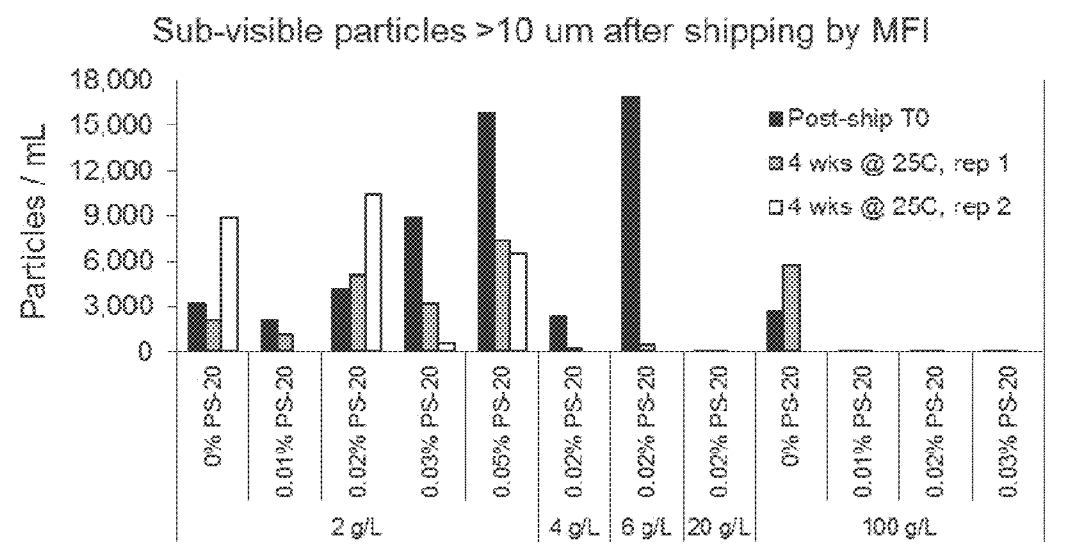
FIG. 7. Sub-visible particle counts >10 μm, aspect ratio filtered to remove silicone oil droplets. The data compares SVP counts just after shipping to those after 1 month of storage at 25° C. High counts are seen for low protein concentrations, independent of PS-20.

One mL of sample was filled into a platform PFS with 0.4 mg of silicone oil. The samples were shipped, stored at 5° C., 25° C., and 40° C. and tested over two months by visual inspection, MFI, and HIAC. Results are presented in FIG. 7.

The plot shows sub-visible particle counts from MFI after 1 month of storage at 25° C. Sub-visible particle counts from HIAC or after storage at other temperatures showed similar trends to the data set shown. Visual inspections did not indicate high visible particle counts for any of the samples except the one containing calcium chloride. The high protein concentration solutions (>20 g/L) were robust to shipping as long as some PS-20 is present. Therefore, the trehalose formulation was used in long term stability studies for 20-100 g/L solution.

The shipping data verified that the low concentration formulations were not robust, as observed by the high and highly variable sub-visible particle counts. The data also showed that the issue was not solved by polysorbate alone, therefore the low concentration solutions needed to be reformulated.

d. Reformulation of Low Concentration DS

The low concentration reformulation screens were stressed by simulated transportation and tested by MFI. The sub-visible particle counts shown were particles >10 μm, aspect ratio filtered; trends were similar for other particle sizes.

During manufacturing, an unformulated drug substance (UDS) at high concentration (≥100 g/L) containing trehalose will be produced and frozen. Storage of this high concentration intermediate is necessary to enable dilution into various formulations across the 2-100 mg/mL formulation range. Dilution from the UDS will result in some residual trehalose; for uniformity of composition, a single trehalose concentration will be used for the entire low dose range. The buffer and pH were not changed.

Figure 8:
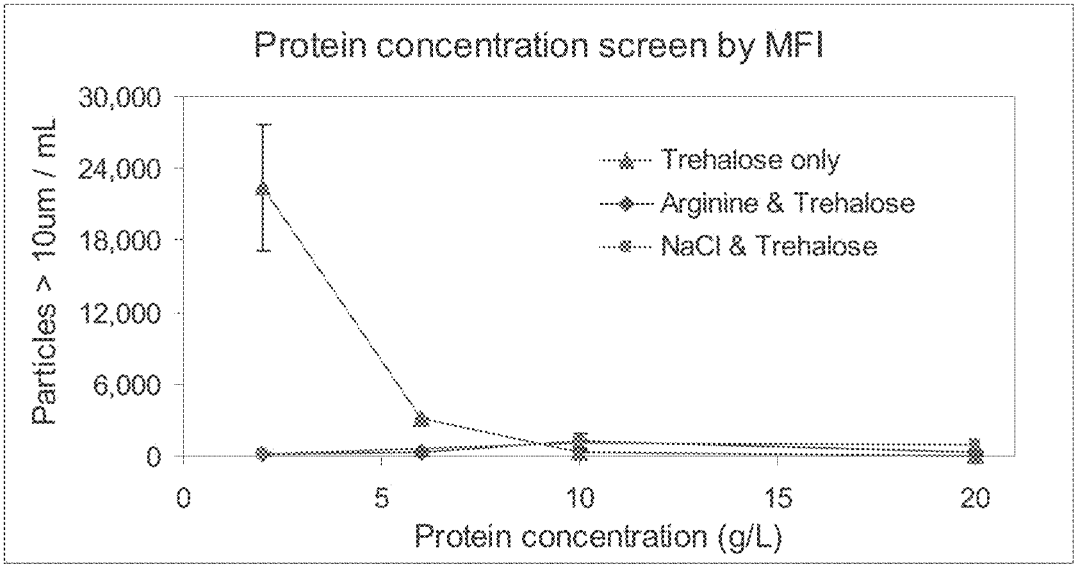
FIG. 8. Particle counts >10 μm by MFI after simulated transportation for varying protein concentrations and formulations. Higher ionic strength formulations are more stable, as are trehalose formulations ≥10 g/L.

The first screen was used to determine the minimum protein concentration where the trehalose formulation was stable, and to determine the effect of increased ionic strength by formulating in 150 mM trehalose with 75 mM arginine HCl or sodium chloride. The results shown below indicate that protein concentrations ≥10 g/L were stable, but for robustness the low concentration range was set at 2-20 g/L. Increasing the ionic strength resulted in more stable solutions with both excipients. See, e.g., FIG. 8.

Figure 9:
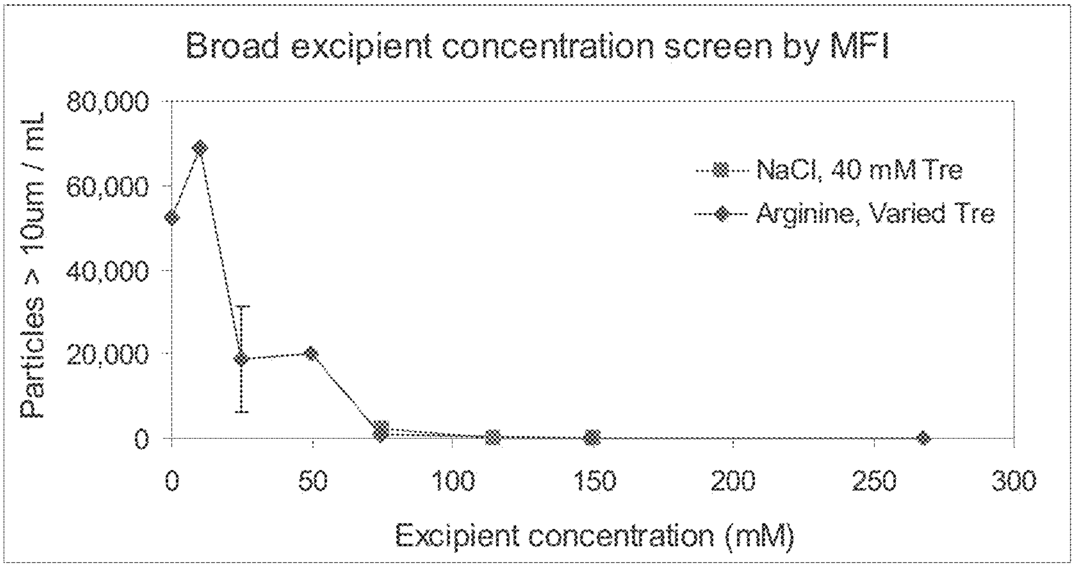
FIG. 9. Particle counts >10 μm by MFI after simulated transportation for 2 g/L protein and varying formulations. The arginine concentration should be >50 mM and the NaCl concentration should be >75 mM.
Figure 10:
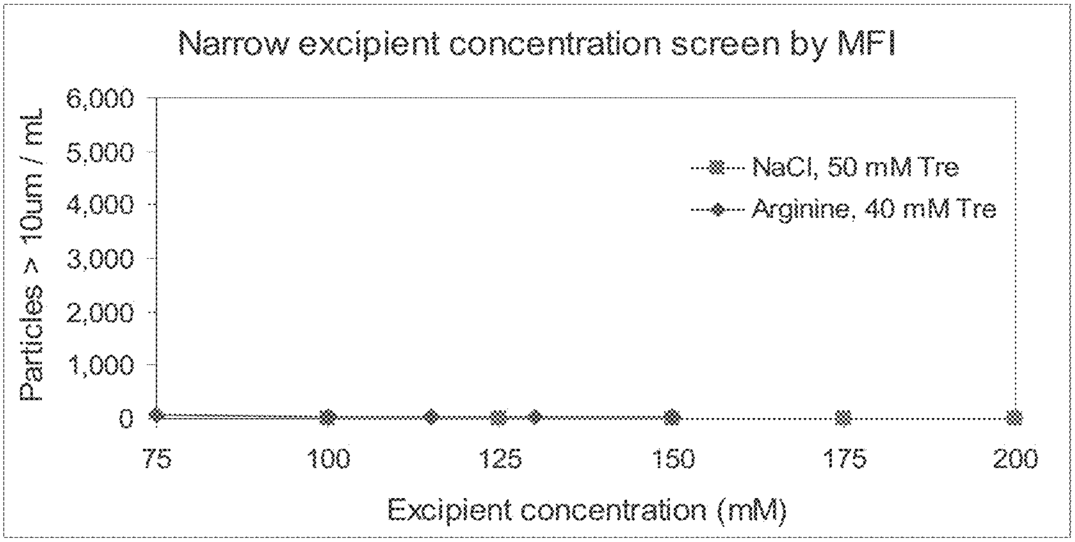
FIG. 10. Particle counts >10 μm by MFI after simulated transportation for 2 g/L protein and varying formulations. Any excipient concentration in this range is acceptable.

The next studies focused on optimizing the arginine or NaCl concentrations; a protein concentration of 2 g/L was used as worst case for all the studies. For each excipient, broad and narrow excipient concentration screens were run with 0.02% PS-20. The initial arginine screen was run with varying amounts of trehalose, where solutions were made by combining 270 mM arginine with 250 mM trehalose. The objective was to maintain the osmolality, but the calculation was done incorrectly (arginine-HCl is bivalent) so the arginine containing solutions were hyper-osmotic. The rest of the excipient concentration screens were done with a constant trehalose concentration of 40 or 50 mM, based on the residual trehalose at 20 g/L after dilution from the 100 g/L stock. The results are provided in FIGS. 9 and 10.

The results of the broad arginine and NaCl screens indicated that the concentration needs to be greater than 50 mM arginine or 75 mM NaCl to produce a stable formulation. The narrow concentration screens of 75-150 mM arginine or 100-200 mM NaCl resulted in low particle counts throughout the entire range. This indicated a concentration in the middle of these ranges should yield a robust formulation; 130 mM was chosen to be iso-osmotic in combination with 50 mM residual trehalose.

Figure 11:
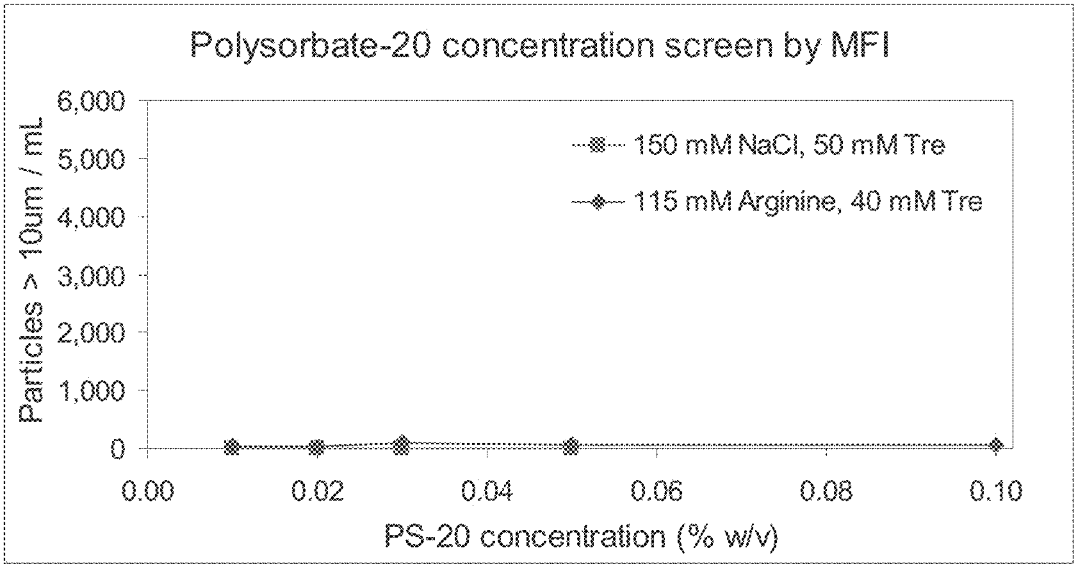
FIG. 11. Particle counts >10 μm by MFI after simulated transportation for 2 g/L protein and varying formulations.

The PS-20 concentration optimization was checked for the new formulations using the same method. These experiments were done concurrently with the narrow excipient concentration screens, so a mid-point concentration was used. The conditions tested were 0.01-0.1% PS-20, 115 mM arginine HCl, 40 mM trehalose and 0.01-0.05% PS-20, 150 mM NaCl, 50 mM trehalose. A couple of samples were tested with 0.02% PS-80, but higher counts resulted than the corresponding PS-20 result (data not shown). The particle counts were low for all of the polysorbate levels tested, indicating that the level does not need to be changed from 0.02% in the new formulations. See, e.g., FIG. 11.

The results of the reformulation for the low concentrations of anti-IL5R indicated either arginine or NaCl were able to stabilize the formulation in the short term. The formulations considered were 130 mM arginine HCl or 130 mM NaCl, with 50 mM trehalose, 20 mM histidine/histidine HCl, 0.02% PS-20, pH 6 for protein concentrations from 2-20 g/L.

e. Vial and PFS Considerations

The three formulations developed above (20-100 mg/mL in trehalose, 2-20 mg/mL in trehalose/arginine, and 2-20 mg/mL in trehalose/NaCl) were appropriate for both vial and PFS configurations. The vial configuration was a 3 cc Schott vial with a 4432/50 West stopper. The highest risk with regard to the vial configuration was the silicone oil level on the stoppers, so the long term stability studies were run with stoppers that have a higher level of silicone oil (0.039 mg/cm$^2$) than those that will be generally be used (0.007-0.024 mg/cm$^2$).

The syringe tested with the anti-IL5R formulation was the platform syringe, a BD 1 mL long PFS with a clipped flange, a staked 29 G thin wall needle, containing 0.4 mg Si oil, and covered with a BD260 rigid needle shield (Catalog #47363119).

f. Long Term Stability Studies

Two long-term stability studies were run to verify the decisions made from screening studies. Stability study #1 investigated the long term stability of the trehalose and arginine/trehalose formulations in PFS and vials. Additionally, PFS comparisons were made which will not be discussed here. Stability study #2 was initiated to provide data from another lot of material for the configurations examined in study #1, and also to investigate the NaCl/trehalose formulation bracket and the impact of fill volume from ½ mL to 1 mL in PFS and vials.

i. Stability Study #1: Stability of Anti-IL5R PFS Presentations

Stability studies were run in syringes with vials as a control. Each of the end points of the formulation brackets was tested in each primary container. The syringe tested was the platform Hypak™ for Biotech; this is a BD glass 1 mL long syringe, practically free of tungsten with a 29 G thin wall needle and 0.4 mg of silicone oil. The vials used were 3 cc Schott vials with West 4423/50 stoppers and over-seals.

The formulations filled are the following:

2 and 20 mg/mL anti-IL5R antibody, 125 mM arginine HCl, 50 mM trehalose, 20 mM histidine/histidine HCl, 0.02% PS-20, pH 6; and 20 and 100 mg/mL anti-IL5R antibody, 250 mM trehalose, 20 mM histidine/histidine HCl, 0.02% PS-20, pH 6.

A. Purity of Anti-IL5R Pre-Filled Syringe Presentations

Figure 12A:
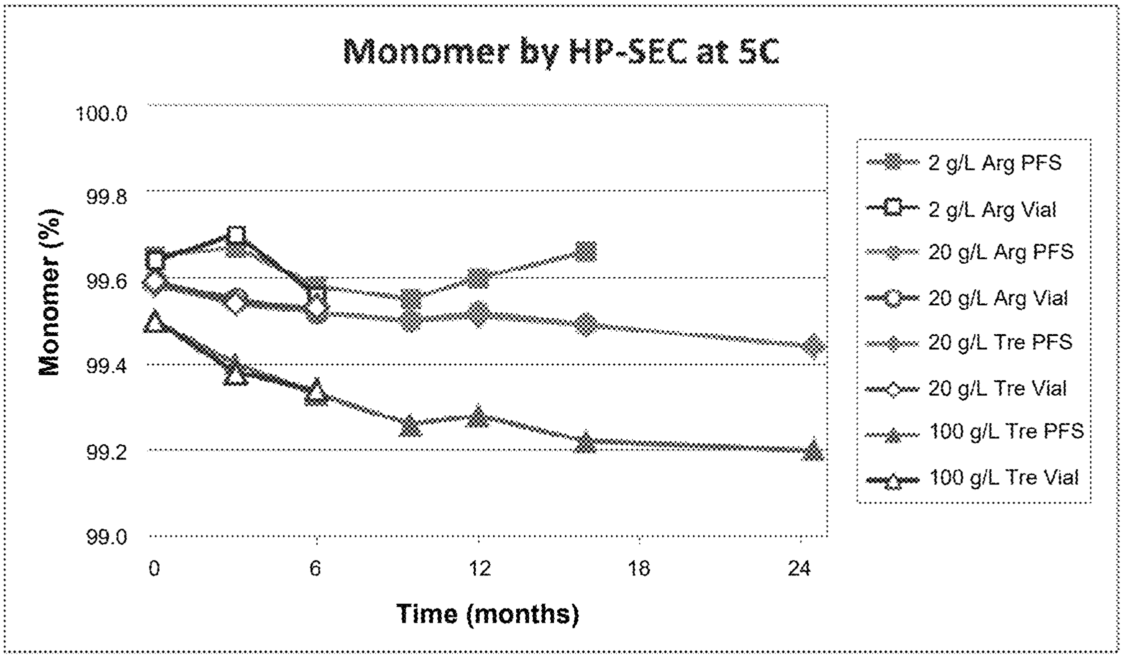
FIG. 12(A-C). Monomer loss for the 2 mg/mL, 20 mg/mL and 100 mg/mL formulations in vials and pre-filled syringes are shown. All of the PFS show similar loss to the vials and to one another.

There was no significant effect of the primary container on monomer loss for any formulations. Some impact of protein concentration was observed, but the monomer loss rate was consistently low. See FIG. 12A.

B. Particle Analyses of Anti-IL5R Pre-Filled Syringe Presentations

Figure 12B:
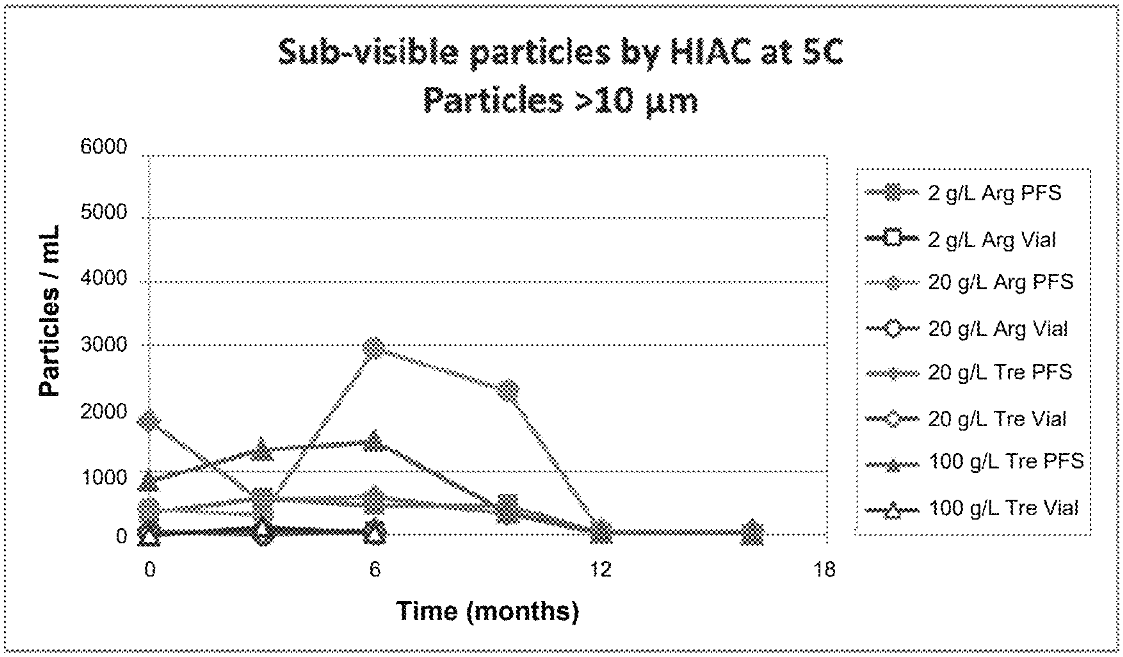
Figure 12C:
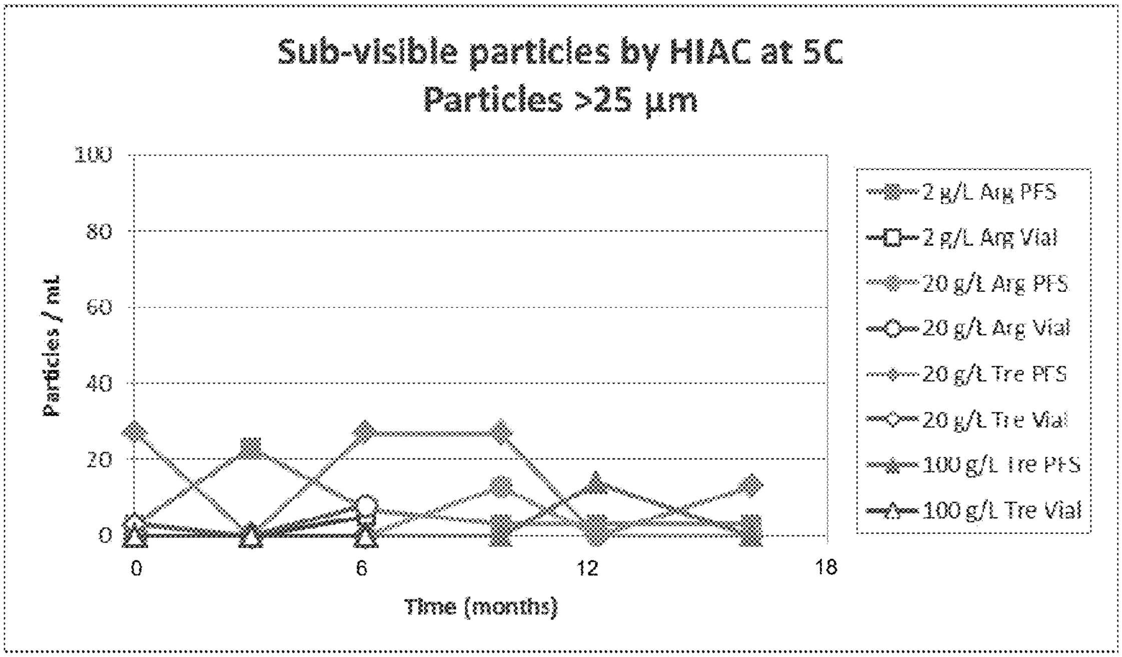

Particle formation was thought to be the main degradation route for anti-IL5R so it was thought to play a large role in determining a suitable PFS. Sub-visible particle measurements by HIAC showed an increase in the number of particles in the PFS, likely due to silicone oil droplets (See, FIGS. 12B and 12C). However, the total particle counts remain well below the USP limits of 6000 particles >10 μm/mL and 600 particles >25/mL for all configurations. MFI was used as an orthogonal method and showed similar results, though less of a difference was observed between containers since silicone oil droplets can be filtered out of the results in the MFI software.

ii. Summary of Stability in Hypak™ for Biotech Syringes at 5° C.

TABLE 1 shows a summary of the stability data (Stability Study #1) available for anti-IL5R in the Hypak™ for Biotech syringes at 5° C. up to 16 months for arginine formulations and 24 months trehalose formulation. Visual particles were detected which lead to a reduction in the PS-20 concentration from 0.02% to 0.006%. No other high risks were identified, though sub-visible particle counts were variable.

TABLE 1

| Assay | | Range of results for all time points tested | | | |
|---|---|---|---|---|---|
| | | 2 mg/mL Arg | 20 mg/mL Arg | 20 mg/mL Tre | 100 mg/mL Tre |
| Appearance (Visible Particles, worst observation) | | <STD 1 | =STD 4 | =STD 2 | <STD 3 |
| HIAC | >10 μm | <590 | <3,000 | <1,800 | <2,000 |
| (Particles/mL) | >25 μm | <30 | <20 | <30 | <60 |
| MFI | >10 μm | <110 | <2,200 | <1,400 | <1,700 |
| (Particles/mL) | >25 μm | <50 | <100 | <60 | <480* |
| SEC (Mon. Loss %/yr) | | 0% | 0.1% | 0.1% | 0.2% |
| RP (% Fragment) | | ≤2.0% | ≤1.8% | ≤1.9% | ≤1.9% |
| Functionality Forces by Instron (Break-loose and Glide Force) | | <6N | <7N | <7N | <12N |

TABLE 1-continued

| Assay | | Range of results for all time points tested | | | |
|---|---|---|---|---|---|
| | | 2 mg/mL Arg | 20 mg/mL Arg | 20 mg/mL Tre | 100 mg/mL Tre |
| BioAssay (Potency %) | | 93-116% | 92-103% | 95-111% | 88-99% |
| BioAnalyzer | Reduced | | Consistent with Ref. Std. | | |
| | Non-Reduced | | Consistent with Ref. Std. | | |
| cIEF | | | Consistent with Ref. Std. | | |

Stability summary of anti-IL5R in multiple formulations in Hypak for Biotech syringes at 5° C. for 16 months. Appearance results included particles, which were mitigated by reducing the PS-20 concentration (covered in a separate report). Sub-visible particle results were variable, but no trends were observed. All other results are within expectations for a stable product.* iii. Stability Study #2

Stability study #2 was a bracketed stability study in pre-filled syringes and vials, designed to decide the low dose formulation and the fill volume, and to verify placebo stability.

The previous stability study used to choose the PFS had a fill volume of 1 mL only. However, there were a number of potential benefits to a lower fill volume including reduced pain on injection, a smaller lump under the skin, faster administration, and less leakage from the administration site.

Figure 13:
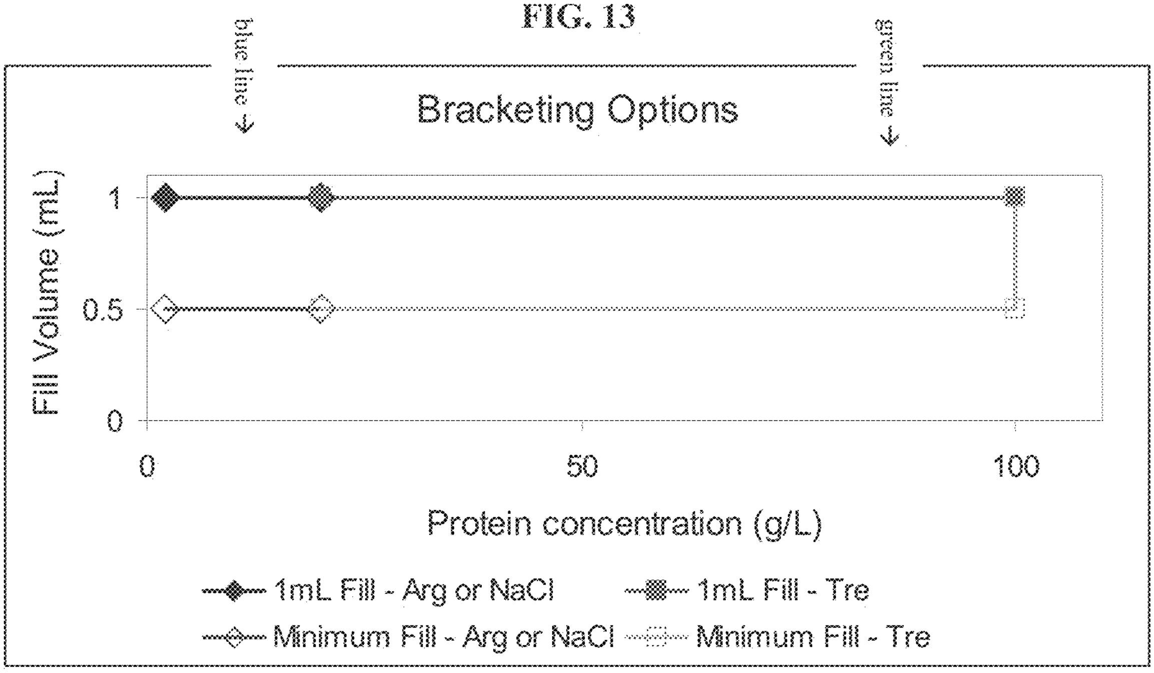
FIG. 13. A graphical representation of the bracketing strategy is shown. Blue indicates the arginine or NaCl containing formulations. Green indicates the trehalose formulation. Data points are prepared samples and lines indicate the bracketed options available to achieve intermediate doses.

The bracketing strategy for the 1 mL fill option was two brackets of protein concentration, 2-20 g/L for the low dose and 20-100 g/L for the high dose. The same brackets for a ½ mL fill covered the dose range of 1-50 mg, and also required a fill volume bracket of 100 g/L from ½-1 mL for the 50-100 mg dose. This is shown graphically in FIG. 13 for clarity. In both cases, the lowest dose bracket was studied in both the arginine and NaCl based formulations.

The drug substances and placebos filled were the following:

All solutions: 20 mM Histidine/Histidine HCl, 0.02% PS-20, pH 6.0

2 Arg/20 Arg: 2 or 20 g/L anti-IL5R, 125 mM Arginine HCl, 50 mM Trehalose

2 NaCl/20 NaCl: 2 or 20 g/L anti-IL5R, 130 mM NaCl, 50 mM Trehalose

20 Tre/100 Tre: 20 or 100 g/L anti-IL5R, 250 mM Trehalose

Arg Placebo: 125 mM Arginine HCl, 50 mM Trehalose

NaCl Placebo: 130 mM NaCl, 50 mM Trehalose

Tre Placebo: 250 mM Trehalose

The 1 mL fill volume configuration was not placed on test for any of the vial configurations or the placebo in PFS in order to reduce the total size of the study, since the ½ mL fill volume was the most likely worst-case configuration due to the higher surface area to volume ratio.

All of the samples were shipped and then placed on stability at 5, 25, and 40° C. The vials were stored inverted during stability to maximize contact with the stopper. At the time the visible particles were discovered in older studies, 6 weeks of data had been collected for this stability study. Additionally, particles were observed in the NaCl formulation between the 3 and 6 month time points of this study (data not shown), leading to the NaCl formulation being rejected in favor of the arginine formulation.

The additional formulation work required to mitigate the formation of visible particles is described in the examples that follow and resulted in a decrease of the polysorbate-20 concentration from 0.02% to 0.006%. No other stability concerns were observed for this formulation, and no significant impact of container or fill volume was observed. One year of stability data is summarized in the FIG. 14, including visible particle scores, purity loss by SEC, particle counts by HIAC, and potency (not all configurations were tested at all time points).

Conclusion of Example 1

Formulation screening was carried out using various stress methods including freeze/thaw, agitation, silicone oil spiking, and accelerated stability. Long-term stability was used to verify the results of the screening studies. The phase 2b trehalose formulation was successful for liquids at high concentration with an increased polysorbate concentration, but showed instability when extended to liquids at low concentrations, primarily through the formation of sub-visible particles. The low concentration range was reformulated by increasing the ionic strength with either arginine hydrochloride or sodium chloride, resulting in a stable solution.

In order to cover the wide range of possible doses (2-100 mg), the three potential formulation brackets were the following:

2-20 g/L, 130 mM arginine hydrochloride, 50 mM trehalose dihydrate, 20 mM histidine/histidine hydrochloride, 0.02% polysorbate-20, pH 6.0;

2-20 g/L, 130 mM sodium chloride, 50 mM trehalose dihydrate, 20 mM histidine/histidine hydrochloride, 0.02% polysorbate-20, pH 6.0; and 20-100 g/L, 250 mM trehalose dihydrate, 20 mM histidine/histidine hydrochloride, 0.02% polysorbate-20, pH 6.0.

Long-term stability of up to 24 months indicates all three formulations were stable at 2-8° C. with respect to agitation, relatively insensitive to silicone oil, and compatible with vials and PFS. Additionally, minimal degradation was observed at elevated temperatures. Continued observations of the two low concentration formulations eliminated the NaCl option due to increased visible particle formation compared to the arginine option, resulting in two formulation brackets. Data indicated pre-filled syringes are an acceptable primary container with either a 1 mL or ½ mL fill volume. Visible particle formation remained a problem with these formulations, as addressed in the following examples.

Example 2—Particle Formation in Anti-IL5R Formulations

Visible particles were detected in aqueous formulations of anti-IL5R in both vials and PFS in previous long term stability studies, with the first incidence of detection at the 6 month time point (data not shown). A study was conducted to mitigate visible particle formation in an anti-IL5R antibody formulation comprising polysorbate 20 (PS-20) stored for an extended period of time. The following example describes a long term study of formulations comprising various PS-20 and protein concentrations to verify the importance PS-20 concentration has in mitigating particle formation. This study resulted in an acceptable range of 0.002-0.01% PS-20.

Abbreviations and Definitions

| Abbreviation | Definition | Abbreviation | Definition |
|---|---|---|---|
| cIEF | Capillary Isoelectirc Focusing | MFI | Micro-Flow Imaging |
| DLS | Dynamic Light Scattering | PS | Polysorbate |
| DP | Drug Product | PFS | Pre-filled syringe |
| DS | Drug Substance | RP | Reverse Phase Chromatography |
| FC | Flow Cytometry | SEC | Size Exclusion Chromatography |

| Abbreviation | Definition |
|---|---|
| Arg | Arginine formulation: 130 mM arginine HCl, 50 mM trehalose dihydrate, 20 mM histidine/histidine HCl, pH 6.0, various PS-20 |
| Tre | Trehalose formulation: 250 mM trehalose dihydrate, 20 mM histidine/histidine HCl, pH 6.0, various PS-20 |

Preliminary Studies

Particle formation was detected in the long term stability studies described in Example 1. However, the particles were extremely small and appear more like a cloud than individual particles. In order to see the particles, the samples were inspected close to the light source. Since the particles were dissimilar to the ones in the vial and PFS standard sets, the samples were compared to each other as well as the standards at each time point.

Particles were first detected at the 6 month time point in 100 g/L Tre vials with 0.02% PS-20.

Six months and 11 month old samples were compared in (1) vials and (2) pre-filled syringe (PFS). Both studies showed that particle formation was more severe in vials than PFS, though PFS standards weren't available at the time so a numerical comparison is not available. Samples from PFS were decanted and injected into vials for appearance testing. No more particles were observed in these vials, which verify that the difference is not a path length effect. In trehalose formulations, this vial-to-PFS difference is more significant than in arginine formulations.

A comparison of various PS-20 concentrations (0, 0.01, 0.02 and 0.03%) in 100 g/L Tre formulations in both vials and PFS after shipping was made. The lower PS-20 concentrations of 0 and 0.01% PS-20 were completely free of particles at the 11 month time point. Particles were visible in both the vial and PFS at 0.02% and 0.03% PS-20. At 20 months, the 0 and 0.01% PS-20 PFS and 0% PS-20 vial remained clear but the 0.01% vial had a very small tornado of particles.

In targeted studies, when held close to the light source, particles were clearly visible in the 100 g/L Tre, 0.02% PS-20 vials and PFS, in some cases as early as 3-4 months. At the low concentration (20 g/L) end of the Tre bracket particles formed much more slowly and were only observed in vials at 21 months. No particles have been observed in 20 g/L Tre PFS at any PS-20 concentration, with data available up to 21 months. Particle formation in arginine formulations was somewhat slower, with particles being observed in the high concentration (20 g/L) end of the bracket with 0.02% PS-20 at 6-9 months. Particles have never been observed in the 2 g/L Arg formulation at any PS-20 concentration in either container, with data available up to 16 months.

Accelerated and stressed temperature studies did not provide insight into particle formation. At 40° C., particles did not form at all over the testing period of 3 months. At 25° C., particle formation was similar or slightly reduced compared to 5° C.

This data indicated the high protein concentration ends of the bracket were at high risk for visible particles and the low ends were potentially at risk in the long term. Reducing the PS-20 concentration was investigated to mitigate particle formation. The primary container remained the platform PFS, and vials were used as an early read on particle formation since particle formation in vials was more severe and easier to see.

Investigation of Various PS-20 Concentrations

Figure 15:
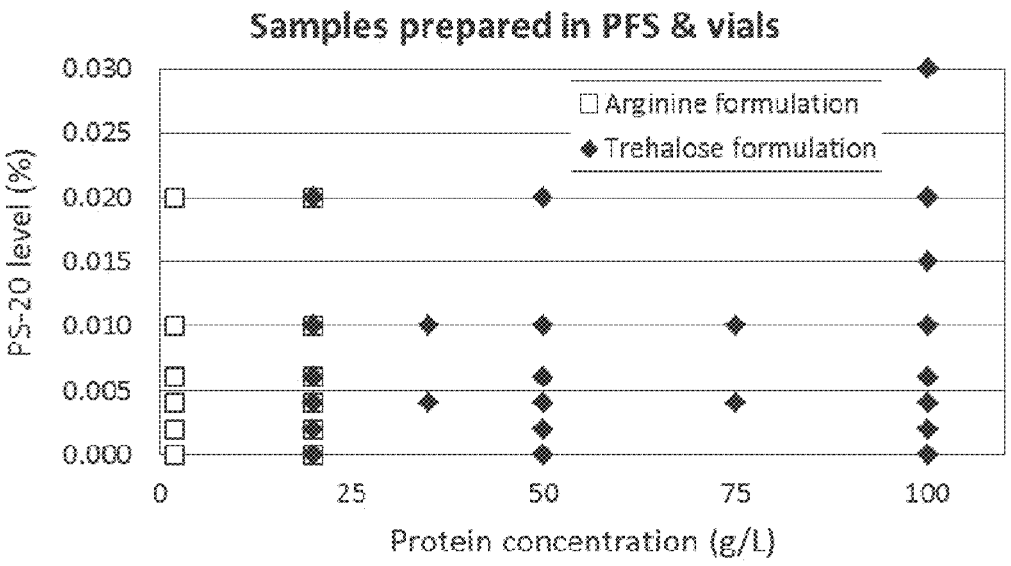
FIG. 15 is a graph showing samples prepared to define the design space as a function of protein and polysorbate-20 ("PS-20") concentrations for both formulation brackets.

An extensive stability study was designed to investigate particle formation in various formulations, various PS-20 concentrations, and various antibody concentrations. All samples were filled into both PFS and vials, shipped twice to a separate location to simulate the distribution process, and placed on stability at 5° C. Appearance testing was performed monthly. SEC, HIAC, and MFI were also tested for a subset of samples at time zero, 3, 6, and 9 months. FIG. 15 shows the samples that were prepared as part of this study.

Figure 16:
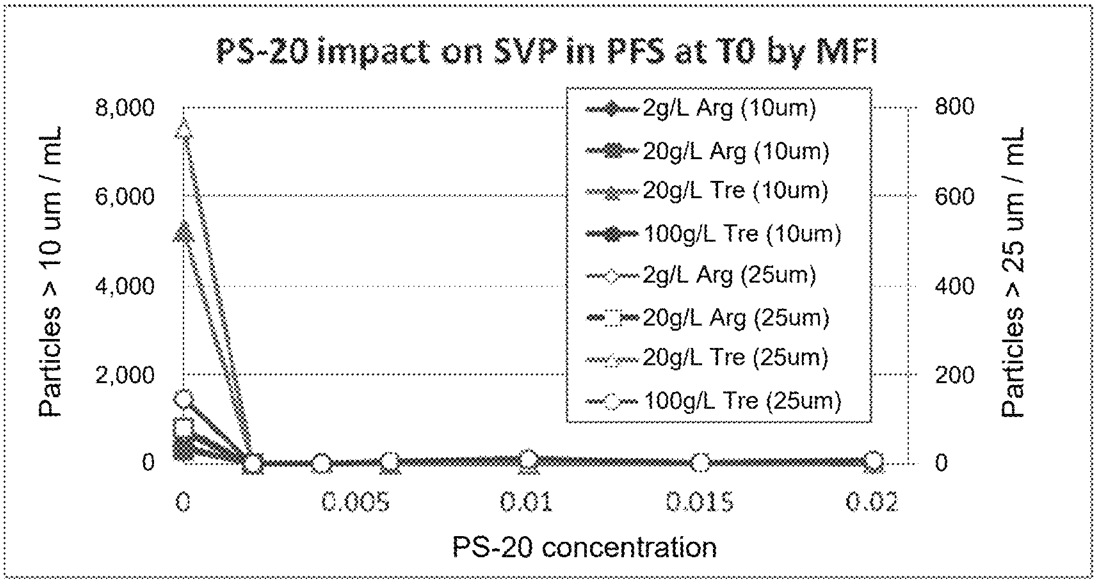
FIG. 16 is a graph of sub-visible particles by MFI at time 0, after shipping. Results show that particles form if no PS-20 is present, but 0.002% PS-20 is sufficient to inhibit particle formation upon shipping.

Without any PS-20, sub-visible particles formed upon shipping as shown by the MFI data in FIG. 16 for PFS at time zero. The lowest tested level of PS-20 (0.002%) or more was sufficient to protect from shipping stress. Additionally, the lowest PS-20 concentration (0.002%) was verified to be sufficient to protect from DS shipping stress in a tank using a scale down model (data not shown here).

Figure 17A:
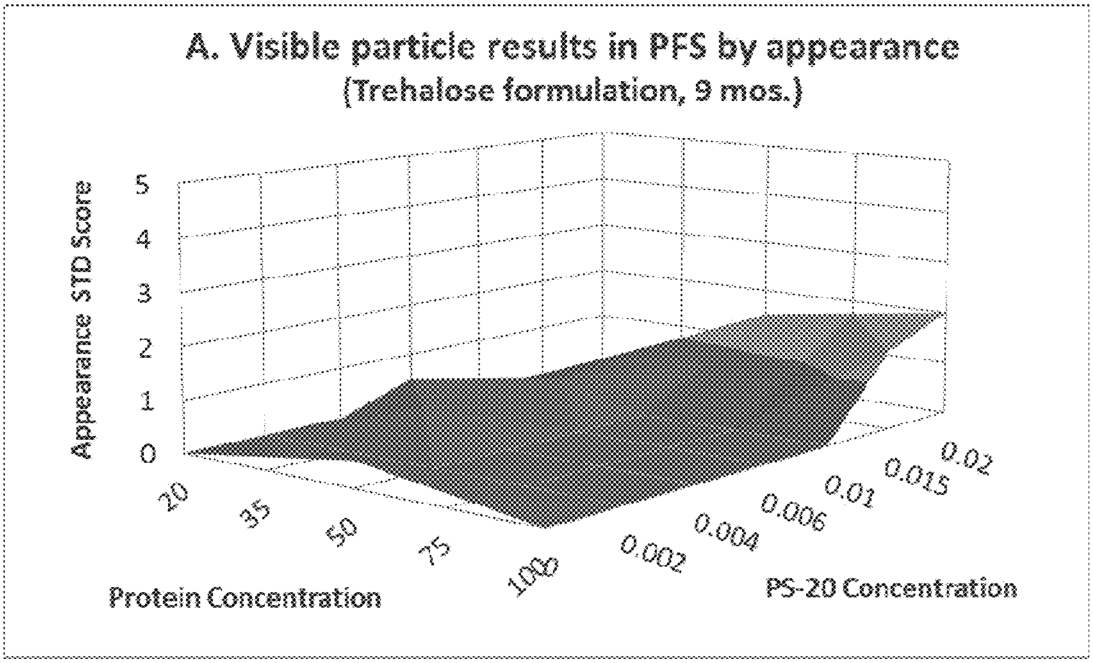
FIG. 17(A-D). Visible particle observations are scored against appearance standards and shown here at the 9 month time point. The observations were made very close to the light. Samples shown include pre-filled syringes ("PFS") containing the trehalose formulation (FIG. 3A), vials containing the trehalose formulation (FIG. 3B), PFS containing the arginine formulation (FIG. 3C), and vials containing the arginine formulation (FIG. 3D). The data supports a target of 0.006% PS-20 and an acceptable range of 0.002-0.01% PS-20 in PFS. Vials are shown as a worst case comparison.
Figure 17B:
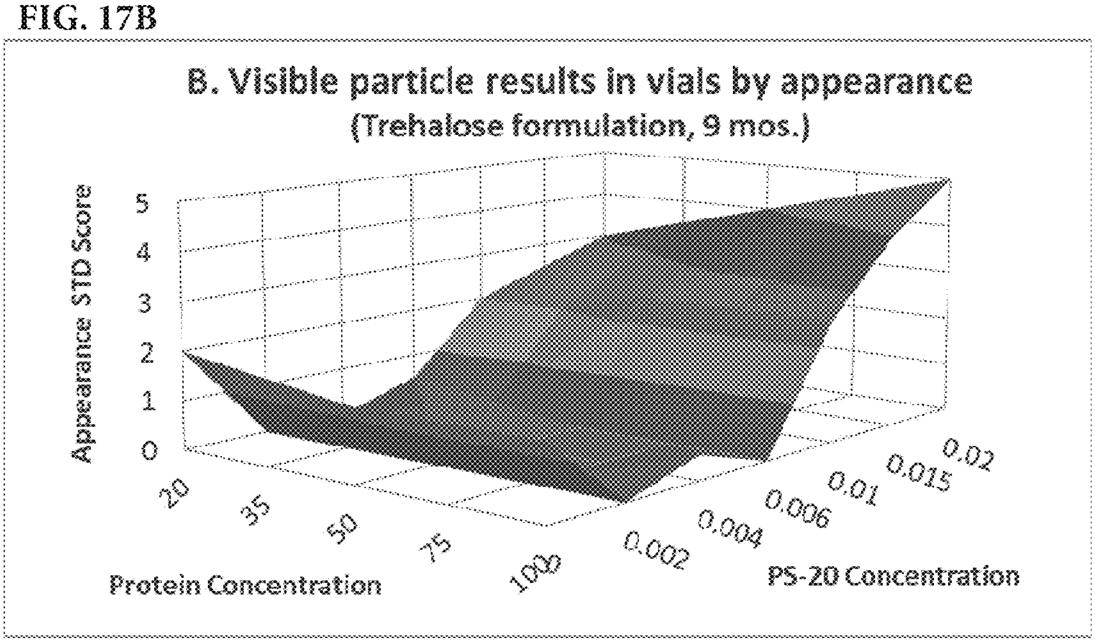

The appearance results for particles showed that there was significant particle formation in vials above 0.01% PS-20, and some particles in PFS at 0.02% PS-20 for both formulation brackets, with fewer particles observed at the lower concentration end of both brackets. See, FIG. 17. The first observations of the particles were at 3 months for 100 g/L Tre and at 6 months for 20 g/L Arg. The figures illustrate the impact of protein and PS-20 concentration on particle formation at the latest time point, 9 months. It is noted that the particle formation observations were all made close to the light source.

The appearance data sets an upper limit on the PS-20 concentration of 0.01% and the sub-visible particle counts set a lower limit of 0.002% (from the available data, actual limit may be lower). The midpoint of this acceptable range (0.006%) was set as the new PS-20 concentration.

Overall stability was verified for PFS for the bracket end samples including up to 9 months of data for 2 g/L Arg and 20 g/L Arg, and up to 18 months of data for 20 g/L Tre and 100 g/L Tre. The following assays were tested:

A. 0.002, 0.006, and 0.01% PS-20: Appearance, HIAC, MFI, and SEC.

B. 0.006% PS-20 only: Instron, BioAssay, BioAnalyzer, RP, and cIEF.

All of the data indicates the new formulation was stable and low risk. A summary of the data is shown in Table 2.

TABLE 2

| Assay | | Results for all samples tested |
|---|---|---|
| Appearance (Visible Particles, worst observation) | | <Std 2 |
| HIAC (Particles/mL) | >10 μm | <640/mL |
| | >25 μm | <30/mL |
| MFI (Particles/mL) | >10 μm | <610/mL |
| | >25 μm | <60/mL |
| SEC (Monomer Loss %/yr) | | 0.0-0.4%/yr |
| RP (% Fragment) | | ≤1.8% |
| Functionality Forces by Instron | Break-loose Force | ≤8.5N |
| | Glide Force | ≤11.8N |
| BioAssay (Potency %) | | 86-109% |
| BioAnalyzer | Reduced | Consistent with Ref. Std. |
| | Non-Reduced | Consistent with Ref. Std. |
| cIEF | | Consistent with Ref. Std. |

The available data from Example 2 indicated a reduction of the PS-20 concentration to 0.006% mitigates particle formation and produced an antibody formulation product that was stable for at least 9 months (arginine formulation) or 18 months (trehalose formulation), with no indications of an upcoming failure.

Example 3

Orthogonal Methods for Particle Detection

The primary method of particle detection and quantification was appearance testing by visual inspection as exemplified in Example 2. Visual inspection was variable for a number of reasons. In general, visual inspection varied due to the innate variability of human perception, leading to different results for different individuals. Due to the very small size of these particles their visibility was highly dependent on the amount of light and they were dissimilar to the particle standards for both vials and PFS. These factors increased the variability of results between time points and between analysts.

Orthogonal methods were investigated to verify the appearance results. The particles formed in trehalose formulations were too small to see individually, so sub-visible particle methods were investigated. The worst case sample (100 g/L, Tre, 0.02% PS-20, vial) from various lots at 2 weeks, and 2, 5, and 9 months old was compared by DLS, FC, HIAC, and MFI.

The DLS was run at 100 g/L, leading to an underestimate of the main peak as expected and unreliability of the all peak sizes. Large peaks were detected for the 2, 5, and 9 month old samples that were 1.4-2.2 μm in size. Although the reported size was not reliable, the presence of the peaks correlated with visible particles. However, neither the reported size of the particles nor the intensity of the particle peak correlated with the visual appearance results.

HIAC results were similar for all of the samples; the particles were not detected.

Figure 18:
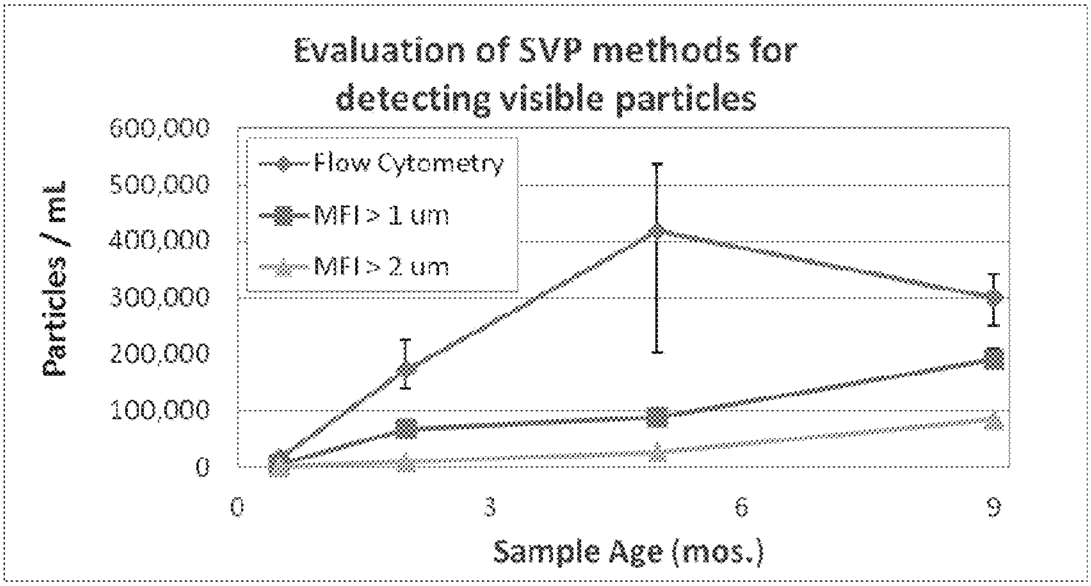
FIG. 18 compares various SVP methods for capturing an increase with sample time, correlating with visible particles. Flow cytometry and small particle counts (>1 and >2 μm) by MFI are able to capture the trend well.

MFI counts for particles >10 μm and >25 μm were similar for all samples. However, MFI counts for particles >1 μm and >2 μm and FC counts trend with the visual appearance results and increase as a function of the sample age. The results for these samples are shown in FIG. 18.

Further experiments indicate that particles >1 μm by MFI provide more reliable trends with visual appearance results than larger particles or FC counts (data not shown).

Similar experiments were run with 20 g/L Arg samples showing visible particles, but none of the orthogonal methods were successful for detecting these particles. The particles formed in arginine formulations appeared much larger than those formed in trehalose and were seen as individual particles, which was likely why they were not detected by sub-visible particle methods.

MFI was used to verify the effect of PS-20 concentration in Example 2. The comparison of MFI and the appearance score are shown in FIG. 19 for Example 2 at the 9 month time point. Along with additional measurements (not shown), the comparison indicated particles were visible when the MFI count exceeded approximately 100,000 particles >1 μm/mL. The MFI results provided added support to the conclusion that particle formation was mitigated by 0.002-0.01% PS-20, especially in PFS. The vial data was considered worst case and was also stable at the target concentration of 0.006% PS-20.

Example 4

Stability Study

Figure 20:
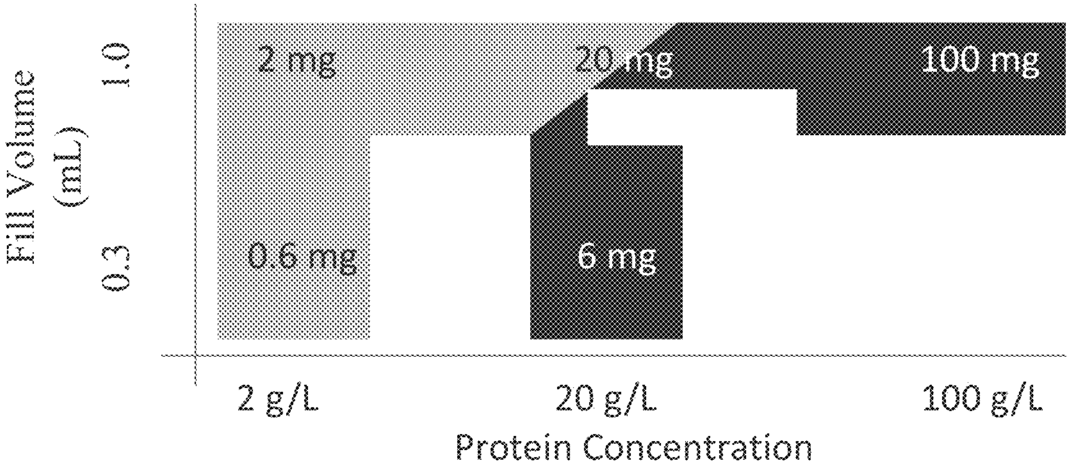
FIG. 20 represents a bracket design as outlined in Example 3 and the lead lot stability study performed in ABC. Orange shaded area indicates the arginine formulation and blue shaded area indicates the trehalose formulation, all with 0.006% PS-20.

An additional stability study was performed to investigate all the configurations of the previous studies with the new target PS-20 concentration of 0.006%, and to add confidence that these formulations are stable. The bracket included a protein concentration bracket as well as a fill volume bracket and is shown graphically in FIG. 20.

The addition of the fill volume bracket increased the range of doses that were covered by the trehalose formulation. These additional configurations reduced the risk associated with the arginine formulation, which was riskier because the particles form more slowly and cannot be detected by orthogonal methods. The samples included in this stability study were:

0, 2, and 20 g/L, 1 mL fill, Arginine formulation, 0.006% PS-20;

0 and 2 g/L, 0.3 mL fill, Arginine formulation, 0.006% PS-20;

0, 20, 50, and 100 g/L, 1 mL fill, Trehalose formulation, 0.006% PS-20; and 0 and 20 g/L, 0.3 mL fill, Trehalose formulation, 0.006% PS-20.

The samples were shipped to an off-site location twice to simulate the distribution process and then placed on stability at 5° C., 25° C., and 40° C.

Nine months of data was collected for the arginine formulations and twelve months of data has been collected for the trehalose formulations. The results were consistent with historical data and no particles were observed in these samples up to this point. Further, no trends in sub-visible particles over time have been observed, although a few moderately high outliers have occurred. The range of results for all of the assays is shown in Table 3.

TABLE 3

| Assay | | Range of results for all samples tested 5° C. (9 mos. Arg or 12 mos. Tre formulations) | 25° C. (6 mos.) | 40° C. (1 mo.) |
|---|---|---|---|---|
| Appearance (Visible Particles, worst observation) | | =Std 0 | <Std 1 | =Std 0 |
| HIAC (Particles/mL) | >10 μm | <2,400/mL | <1,900/mL | <1,900/mL |
| | >25 μm | <110/mL | <110†/mL | <100/mL |
| MFI (Particles/mL) | >10 μm | <100/mL | <700/mL | <50/mL |
| | >25 μm | <50/mL | <40/mL | <10/mL |
| SEC (Monomer Loss) | | 0-0.3%/yr | 0.1-0.6%/mo | 2.2-3.5%/mo |
| RP (% Fragment) | | ≤1.7% | ≤3.6% | ≤4.4% |
| Functionality Forces by Instron (Break-loose and Glide force) | | ≤11.7N | Not tested | Not tested |
| BioAssay (Potency %) | | 84-122% | 83-113% | 83-110% |
| BioAnalyzer | Reduced | Consistent with Ref. Std. | | |
| | Non-Reduced | Consistent with Ref. Std. | | |
| cIEF | | Consistent with Ref. Std. | | Inconsistent with Ref Std. at 1 mo. |

†43 of 44 measurements fell in this range, but one outlier of 347 particles/mL was also measured.

The data supported the recommendation of this formulation bracket for the full dose range. The trehalose bracket was lower risk than the arginine bracket and was recommended for doses as low as 6 mg.

Conclusion of Example 2-4

Particle observations in previous long-term stability studies led to an investigation into formulation variables that could be altered to improve stability. The key variables, protein and polysorbate concentration, were tested and analyzed. Based on the data presented above, an allowable range of polysorbate from 0.002% to 0.01% and a target of 0.006% was determined to be optimal formulations for the anti-IL5R antibody formulation. This observation was supported by two stability studies with 18 and 12 months of available data, primarily by visual appearance testing.

It was also observed that the trehalose formulation could be used rather than the arginine formulation in the 6-20 mg range by using a 0.3-1.0 mL volume bracket at 20 mg/mL. The trehalose formulation was found to be more predictable than the arginine formulation due to the larger data set and better detection.

Example 5

Figure 21:
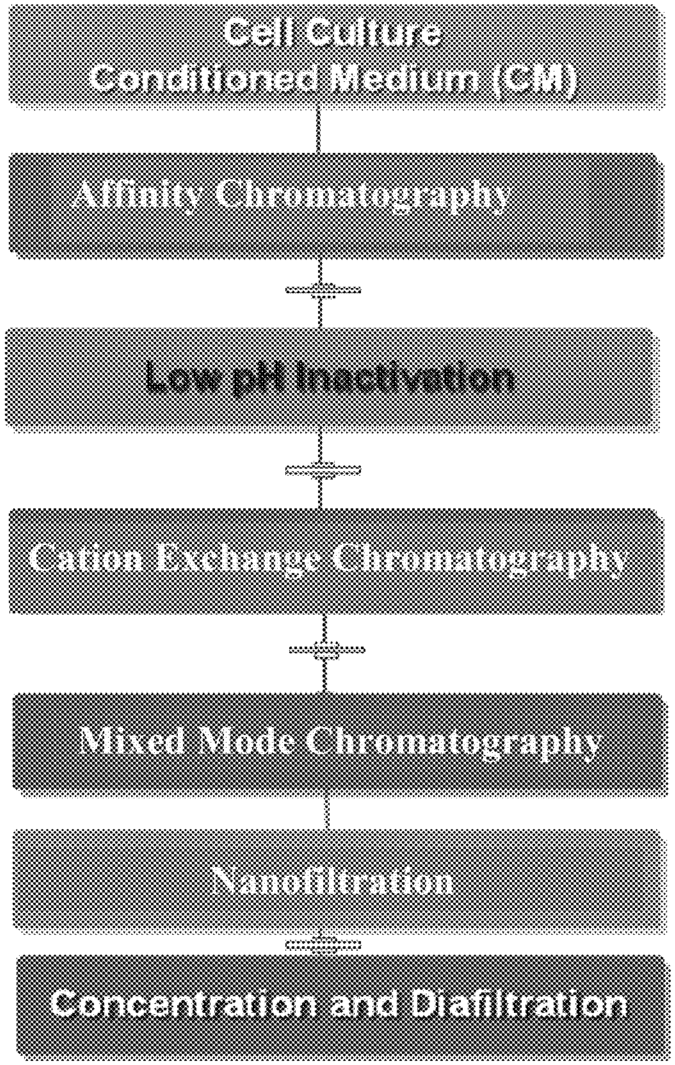
FIG. 21 represents one schematic example of an antibody purification process.

Additional purification development was undertaken focused on reducing host cell protein (HCP) to determine the effect of HCPs on particle formation. Anti-IL5R was purified as outlined in FIG. 21

Figure 22:
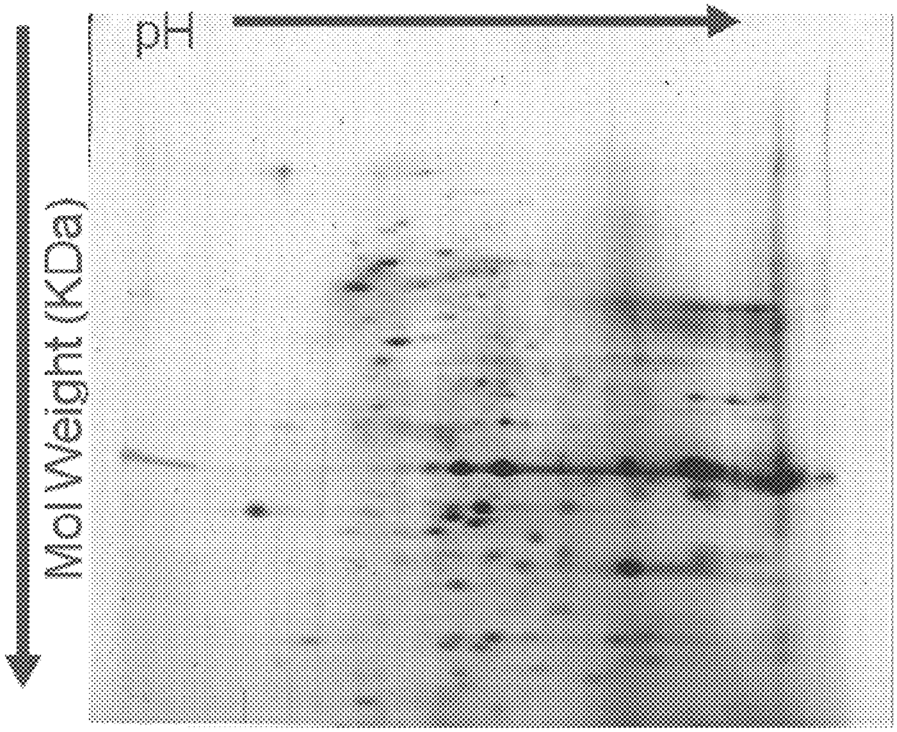
FIG. 22 represents 2D gel analysis of the flow-thru of a Protein-A column used in the purification of anti-IL5R antibody.

2D gel analysis of the flow-thru of the Protein A column indicated there were several protein species present. See, e.g., FIG. 22. The major impurities, as determined by reverse phase mass spectroscopy (RP-MS) included about 60% Fab fragment, about 5% light chain (LC) and fragments, and about 40% non-anti-IL5R related host cell proteins (HCP). The non-anti-IL5R related HCPs included glutathione S-transferase (GST), fructose-biphosphate aldolase, and transaldolase.

The flow-thru of the Protein A column was further passed through a Protein L column to further separate (1) the Fab fragments from (2) the non-anti-IL5R HCPs. It was found that some material in the non-anti-IL5R HCPs was responsible for particle formation, and not the Fab fragments (data not shown).

To determine which of the major HCPs was responsible for particle formation, GST was first investigated. The role of GST in particle formation was investigated by (1) selective removal of GST to determine effect on particle formation, (2) analysis of particle pellets to determine the presence of GST in the pellet, and (3) adding GST to anti-IL5R formulations to determine effect on particle formation.

Preliminary evidence of specific removal of GST using an affinity matrix made from a glutathione-sepharose conjugate suggested that removal of GST resulted in reduced particle formation (data not shown). Analysis of pellets formed from Protein A flow-thru indicated high concentrations of GST in the pellets (data not shown).

GST was added (i.e., spiked) to purified anti-IL5R formulations lacking particles to determine the effect of GST on particle formulations. GST was obtained from a commercial source (Prospec). GST was added to a formulation comprising 50 mg/mL anti-IL5R, 20 mM histidine-HCl buffer, 9% (w/v) trehalose, 0.02% PS-20, pH 6.0, resulting in GST concentrations of 3.8 μg/mg and 7.6 μg/mg. The samples were incubated at 38-42° C. Particles were observed by placing the samples on a light box. The incubation time required to observe particle formation was dependent on the level of GST present. For both the 3.8 μg/mg and 7.6 μg/mg spiked GST samples, particles were observed after 24 hours at 38-42° C. (data not shown).

These results suggested that spiking GST into anti-IL5R formulations causes particle formation in the anti-IL5R formulation.

Example 6

GST activity in various anti-IL5R formulations purified by various means was investigated. As a preliminary matter, an activity assay for GST (BioVision) was used to determine GST concentrations to form a standard curve. GST catalyzes the formation of the thiol group of glutathione (GSH) to electrophilic compounds such as 1-chloro-2,4-dinitrobenzene (CDNB) for form a GS-DNB conjugate which is detected at 340 nM. Thus, the increased in absorption at 340 nM is directly proportional to the GST activity. Using this assay, the concentration of GST was determined for various anti-IL5R formulations (Samples A-J) purified using various procedures. The correlation between GST concentration and particle formation was noted. The results are provided in Table 4.

TABLE 4

| Sample | GST concentration | Particle Description |
|---|---|---|
| A | 188.4 | High number of particles (the most) |
| B | 0.422 | Practically free* |
| C | 2.074 | Practically free* |
| D | 1930.5 | High number of particles |
| E | 1950.6 | High number of particles |
| F | 1774.2 | High number of particles |
| G | 40.6 | Particle forming |
| H | 1.073 | Some particles |
| I | <LLOQ | Free of particles |
| J | 5.416 | Particle forming |

*Some, but not many, particles.
LLOQ = lower limit of quantification.

This evidence confirms that the presence of GST correlates with the formation of particles.

Example 7

Various purification columns were investigated to identify the most efficient method of reducing the GST concentration in an anti-IL5R formulation. See Table 5. GST concentration was determined as outlined in Example 7.

TABLE 5

| Description | GST Conc. (μg/ml) |
|---|---|
| CM Product | 5.935 |
| HA product | 1.255 |
| MabSelect Sure Elut. Product | <LLOQ |
| CaptoAdhere Product | <LLOQ |
| CEX Product* | 9.228 |
| CEX Product* | 21.081 |

*GST concentrations of two separate batches of anti-IL5R antibodies were determined.

Table 5 suggests that both the Protein A column (MabSelect Sure) and the mixed mode chromatography column (CaptoAdhere) were successful at reducing the concentration of GST below a detectable level during purification of the anti-IL5R antibody.

Example 8

The presence of GST in other antibody preparations was investigated. The presence of particles in those antibody preparations was also investigated. The results are presented in Table 6, with comments.

TABLE 6

| Antibody formulation | Active GST Detected? | Trend with Particle Formation? | Comments |
|---|---|---|---|
| Anti-IL5R | Yes | Yes | N/A |
| A | Yes | N/A | Insufficient particle data to determine trend |
| B | No (except 1 sample) | No | Suggests that GST may not be the cause of particle formation for this Ab. |
| C | Yes | N/A | Active GST, but no particle formation |
| D | Yes | N/A | Insufficient Particle data to determine trend |

All of the various embodiments or options described herein can be combined in any and all variations. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. An aqueous antibody formulation that has not been subjected to lyophilization comprising:

a. about 30 mg/ml of an antibody, wherein the antibody comprises a heavy chain variable region and a light chain variable region, wherein the heavy chain variable region comprises the Kabat-defined CDR1, CDR2, and CDR3 sequences of SEQ ID NOs: 5-7, and wherein the light chain variable region comprises the Kabat-defined CDR1, CDR2, and CDR3 sequences of SEQ ID NOs: 8-10, b. about 0.002% to about 0.006% w/v polysorbate-20, c. a buffer, wherein the buffer concentration is about 10 mM to about 30 mM, and d. an excipient, wherein the excipient concentration is about 200 mM to about 400 mM, wherein the antibody formulation has a pH of about 5.5 to about 6.5, and wherein storage of the antibody formulation at 23° C. to 27° C. for 3 months results in degradation of less than 5% of the antibody as determined by high performance size exclusion chromatography (HPSEC).

2. The antibody formulation of claim 1, wherein the excipient is selected from trehalose, sucrose, NaCl, and arginine.

3. The antibody formulation of claim 2, wherein the excipient is trehalose.

4. The antibody formulation of claim 1, wherein the buffer comprises histidine, acetate, glycine, phosphate, or citrate.

5. The antibody formulation of claim 4, wherein the buffer comprises histidine and the buffer concentration is about 15 mM to about 30 mM.

6. The antibody formulation of claim 1, wherein storage of the antibody formulation at 23° C. to 27° C. for 6 months results in degradation of less than 5% of the antibody as determined by HPSEC.

7. A pharmaceutical unit dosage form suitable for parenteral administration to a human which comprises the antibody formulation of claim 1 in a suitable container.

8. The pharmaceutical unit dosage form of claim 7, wherein the suitable container is a pre-filled syringe.

9. The pharmaceutical unit dosage form of claim 8, wherein the pre-filled syringe comprises a needle.

10. The pharmaceutical unit dosage form of claim 9, wherein the needle is a 29 G thin wall needle.

11. A pre-filled syringe comprising the antibody formulation of claim 1.

12. A kit comprising the antibody formulation of claim 1.

13. The antibody formulation of claim 1, wherein the antibody formulation is essentially free of particles.

14. The antibody formulation of claim 1, wherein the antibody formulation is essentially free of active glutathione S-transferase (GST).

15. The antibody formulation of claim 1, wherein the formulation comprises about 20 mM buffer comprising histidine, about 250 mM excipient wherein the excipient is trehalose, and about 0.006% w/v of polysorbate-20.

16. The antibody formulation of claim 1, wherein the formulation comprises about 0.003% w/v polysorbate-20.

17. The antibody formulation of claim 1, wherein the formulation comprises about 0.005% w/v polysorbate-20.

18. The antibody formulation of claim 1, wherein the formulation comprises about 0.006% w/v polysorbate-20.

19. The antibody formulation of claim 6, wherein the excipient is selected from trehalose, sucrose, NaCl, and arginine.

20. The antibody formulation of claim 19, wherein the buffer comprises histidine, acetate, glycine, phosphate, or citrate.

21. The antibody formulation of claim 20, wherein the excipient is trehalose and the buffer comprises histidine.

22. The antibody formulation of claim 21, wherein storage of the antibody formulation at 23° C. to 27° C. for 3 months results in aggregation of less than 5% of the antibody as determined by HPSEC.

23. The antibody formulation of claim 21, wherein storage of the antibody formulation at 23° C. to 27° C. for 6 months results in aggregation of less than 5% of the antibody as determined by HPSEC.

24. The antibody formulation of claim 18, wherein the excipient is trehalose and the buffer comprises histidine.

25. The antibody formulation of claim 1, wherein the antibody is benralizumab and wherein 97.0% or more of the benralizumab constitutes a single peak as determined by HPSEC.

26. The antibody formulation of claim 15, wherein the antibody is benralizumab and wherein 97.0% or more of the benralizumab constitutes a single peak as determined by HPSEC.

27. The antibody formulation of claim 18, wherein the antibody is benralizumab and wherein 97.0% or more of the benralizumab constitutes a single peak as determined by HPSEC.

* * * * *